United States Patent
Rezania

(10) Patent No.: US 9,593,307 B2
(45) Date of Patent: Mar. 14, 2017

(54) DEFINED MEDIA FOR EXPANSION AND MAINTENANCE OF PLURIPOTENT STEM CELLS

(71) Applicant: Janssen Biotech, Inc., Horsham, PA (US)

(72) Inventor: Alireza Rezania, Horsham, PA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 15/150,349

(22) Filed: May 9, 2016

(65) Prior Publication Data

US 2016/0251615 A1  Sep. 1, 2016

Related U.S. Application Data

(62) Division of application No. 13/787,173, filed on Mar. 6, 2013, now Pat. No. 9,434,920.

(60) Provisional application No. 61/607,706, filed on Mar. 7, 2012.

(51) Int. Cl.
| | |
|---|---|
| C12N 5/00 | (2006.01) |
| C12N 5/02 | (2006.01) |
| C12N 5/0735 | (2010.01) |

(52) U.S. Cl.
CPC ........ *C12N 5/0606* (2013.01); *C12N 2500/05* (2013.01); *C12N 2500/25* (2013.01); *C12N 2500/36* (2013.01); *C12N 2500/38* (2013.01); *C12N 2501/105* (2013.01); *C12N 2501/115* (2013.01); *C12N 2501/15* (2013.01)

(58) Field of Classification Search
None
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Chen et al., Nat. Methods, 8(5):424-429 (2011).*
Abe, et al., Evidence That PI3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

(Continued)

*Primary Examiner* — Thomas J Visone
(74) *Attorney, Agent, or Firm* — Lois A. Gianneschi

(57) ABSTRACT

The present invention provides methods to promote the proliferation of undifferentiated pluripotent stem cells in defined media. Specifically, the invention provides a defined cell culture formulation for the culture, maintenance, and expansion of pluripotent stem cells, wherein culturing stem cells in the defined cell culture formulation maintains the pluripotency and karyotypic stability of the cells for at least 10 passages. Further disclosed is a cell population, grown under defined media conditions, that expresses OCT4, SOX2, NANOG, and FOXA2.

13 Claims, 20 Drawing Sheets

(56) References Cited

U.S. PATENT DOCUMENTS

| | | |
|---|---|---|
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 2002/0072117 A1 | 6/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivanlou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0241107 A1 | 10/2008 | Copland III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2010/0304481 A1* | 12/2010 | Thomson ............ C12N 5/0606 435/366 |
| 2011/0014703 A1 | 1/2011 | Xu et al. |
| 2011/0151560 A1 | 6/2011 | Xu |
| 2011/0229441 A1 | 9/2011 | Benchoua et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264218 A1 | 10/2012 | Odorico et al. |
| 2013/0189777 A1 | 7/2013 | Rezania |
| 2013/0224156 A1 | 8/2013 | Takahashi et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359671 C2 | 6/2009 |
| WO | WO9219759 A2 | 2/1992 |
| WO | 9847892 A1 | 10/1998 |
| WO | WO9920741 A1 | 4/1999 |
| WO | 0029549 A1 | 5/2000 |
| WO | 0123528 A1 | 4/2001 |
| WO | WO0151616 A2 | 7/2001 |
| WO | WO0181549 A3 | 11/2001 |
| WO | 0246183 A2 | 6/2002 |
| WO | 0246197 A1 | 6/2002 |
| WO | 02086107 A2 | 10/2002 |
| WO | 02092756 A2 | 11/2002 |
| WO | 03026584 A2 | 4/2003 |
| WO | 03029445 A1 | 4/2003 |
| WO | 03033697 A1 | 4/2003 |
| WO | 03042405 A2 | 5/2003 |
| WO | WO03005049 A1 | 6/2003 |

(56) References Cited

FOREIGN PATENT DOCUMENTS

| | | |
|---|---|---|
| WO | 03054169 A1 | 7/2003 |
| WO | 03062405 A2 | 7/2003 |
| WO | 03095452 A1 | 11/2003 |
| WO | 03103972 A1 | 12/2003 |
| WO | WO03102134 A2 | 12/2003 |
| WO | 2004016747 A2 | 2/2004 |
| WO | WO2004011621 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055834 A2 | 4/2013 |
| WO | 2013184888 A1 | 12/2013 |
| WO | 2014152321 A1 | 9/2014 |

OTHER PUBLICATIONS

Ackermann, et al., Molecular Regulation of Pancreatic B-Cell Mass Development, Maintenance, and Expansion, Journal of Molecular Endocrinology, 2007, pp. 193-206, vol. 38.

Adams, et al., Proteasome Inhibition in Cancer: Development of PS-341, Seminars in Oncology, 2001, pp. 613-619, vol. 28, No. 6.

Age-Related Eye Disease Study Research Group, a Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Ali, et al., Exploitation of Protein Kinase C: A Useful Target for Cancer Therapy, Cancer Treatment Reviews, 2009, pp. 1-8, vol. 35.

Allegrucci, et al., Differences between Human Embryonic Stem Cell Lines, Human Reproduction Update, Aug. 26, 2006, pp. 1-18, Advance Access.

Almond, et al., The Proteasome: A Novel Target for Cancer Chemotherapy, Leukemia, 2002, pp. 433-443, vol. 16.

Amit et al., Human Feeder Layers for Human Embryonic Stem Cells, Biology of Reproduction, Jan. 22, 2003, 2150-2156, 68, No. 6, Society for the Study of Reproduction, Inc.

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Dynamic Suspension Culture for Scalable Expansion of Undifferentiated Human Pluripotent Stem Cells, Nature Protocols, Apr. 7, 2011, pp. 572-579, vol. 6, No. 5.

Amit, et al., Feeder Layer- and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of PI3K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Assady, et al., Insulin Production by Human Embryonic Stem Cells, Diabetes, 2001, pp. 1691-1697, vol. 50.

Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.

Baetge, Production of B-Cells from Human Embryonic Stem Cells, Diabetes, Obesity, Metabolism, 2008, pp. 186-194, vol. 10, Supplement 4.

Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.

(56) References Cited

OTHER PUBLICATIONS

Balsam, et al., Haematopoeitic Stem Cells Adopt Mature Haeatopoietic Fates in Ischaemic Myocardium, Nature, Apr. 8, 2004, pp. 668-673, ?, Nature Publishing Group.

Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.

Barclay, et al., The Leucocyte Antigen Facts Book, The Leucocyte Antigen Facts Book, 1997, Textbook, 2[sup] edition, Academic Press.

Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.

Beltrami, et al., Adult Cardiac Stem Cells are Multipotent and Support Myocardial Regeneration, Cell, Sep. 19, 2003, pp. 763-776, vol. 114, Cell Press.

Best, et al., Embryonic Stem Cells to Beta-Cells by Understanding Pancreas Development, Molecular and Cellular Endorinology, 2008, pp. 86-94, vol. 288.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

Bo, et al., Research Progress of Pancreatic Islet Development and Pancreatic Stem Cells, Journal of Clinical Surgery, 2009, pp. 208-210, vol. 17, No. 3.

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini et al, Embryonic Stem Cells in Domestic Animals, Embryonic Stem Cells in Domestic Animals, 2010, 544-550, 74.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation Into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, 3016-3020, 10.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870, D0I10/1095.

Chetty, et al., A Simple Tool ti Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

Chung, et al., Human Embryonic Stem Cell Lines Generated without Embryo Destruction, Cell Stem Cell, 2008, pp. 113-117, vol. 2.

Cohick, et al., The Insulin-Like Growth Factors, Annual Reviews Physiol, 1993, pp. 131-153, vol. 55, Annual Reviews Inc.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Efficient differentiation of human embryonic stem cells to definitive endoderm, Nature Biotechnology, Oct. 28, 2005, Nature Publishing Group.

(56) References Cited

OTHER PUBLICATIONS

D'Amour et al., Production of pancreatic hormone-expressing endocrine cells from human embryonic stem cells, Nature Biotechnology, Oct. 19, 2006, pp. 1392-1401, vol. 24-11, Nature Publishing Group, US.
Damy, et al., Increased Neuronal Nitric Oxide Synthase-Derived NO Production in the Failing Human Heart, Research Letters, Apr. 24, 2004, pp. 1365-1367, vol. 363.
David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
De Rosa, 11-color, 13-parameter flow cytometry: Identification of . . . , Nature, Feb. 1, 2001, 245-248, 7-2, Nature Publishing Group, US.
Dekker, et al., Adhesion of Endothelial Cells and Adsorption of Serum Proteins on Gas Plasma-Treated Polytetrafluoroethylene, Biomaterials, 1991, pp. 130-138, vol. 12.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dufour, et al., Development of an Ectopic Site for Islet Transplantation Using Biodegradable Scaffolds, Tissue Engineering, 2005, pp. 1323-1331 XP002699177, vol. 11, No. 9/10.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, 524-532, 3, Nature Publishing Group, US.
Eguizabal, et al., Embryonic Stem Cells/Induced Pluriptent Stem Complete Meiosis from Human Induced Pluripotent Stem Cells, Stem Cells, 2011, pp. 1186-1195, vol. 29.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Gibco, Solutions for Life Science Research and Drug Discovery, Catalogue Cell Culture Products, 2004-2005, pp. 1-4E, 281406 26 5 27.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittest, Developmental Biology of the Pancreas: A comprehensive Review, Developmental Biology, 2009, pp. 4-35 XP025995041, vol. 326, No. 1.
Gordon Weir, Do stem cells hold the key to creation of a cure for diabetes?, Diabetes Voice, 2008, pp. 29-31, Edition 53, No. 2.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.

(56) References Cited

OTHER PUBLICATIONS

Gregg Duester, Retionoic Acid Synthesis and Signaling During Early Organogenesis, Cell, 2008, pp. 921-931, vol. 134.

Guo, et al., Stem Cells to Pancreatic B-Cells: New Sources for Diabetes Cell Therapy, Endocrine Reviews, May 2009, pp. 214-227, vol. 30, No. 3, The Endocrine Society.

Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.

Hainsworth, et al., Retinal Capillar Basement Membrane Thickening in a Porcine Model of Diabetes Mellitus, Comp Med, 2002, pp. 523-529, vol. 52.

Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.

Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.

Harmon, et al., GDF11 Modulates NGN3+ Islet Progenitor Cell Number and Promotes B-Cell Differentiation in Pancreas Development, Development, 2004, pp. 6163-6174, vol. 131.

Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.

Hasegawa, et al., A Method for the Selection of Human Embryonic Stem Cell Sublines with High Replating Efficiency After Single-Cell Dissociation, Stem Cells, 2006, pp. 2649-2660, vol. 24.

Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.

Hay, et al., Highly Efficient Differentiation of hESCs to Functional Hepatic Endoderm Requires ActivinA and Wnt3a Signaling, PNAS, 2008, pp. 12301-12306, vol. 105, No. 34.

Hebrok, et al., Notochord repression of endodermal Sonic hedgehog permits pancreas development, Genes & Development, Jun. 1, 1998, pp. 1705-1713, vol. 12, Issue 11, Cold Spring Harbor Laboratory Press.

Heinis, et al., HIF1a and Pancreatic Beta-Cell Development, The FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

Heit, et al., Embryonic Stem Cells and Islet Replacement in Diabetes Mellitus, Pediatric Diabetes, 2004, pp. 5-15, vol. 5.

Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.

Henderson, et al., Preimplantation Human Embryos and Embryonic Stem Cells Show Comparable Expression of Stage-Specific Embryonic Antigens, Stem Cells, 2002, pp. 329-337, vol. 20.

Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.

Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.

Herrera, Adult-Insulin- and Glucagon-Producing Cells Differentiate from Two Independent Cell Lineages, Development, 2000, pp. 2317-2322 XP001004766, vol. 127, No. 11.

Herzenberg, et al., Fluorescence-activated Cell Sorting, Scientific American, 1976, 108-117, 234, Scientific American, US.

Hess, et al., Bone Marrow-Derived Stem Cells Initiate Pancreatic Regeneration, Nature Biotechnology, Jul. 2003, pp. 763-770, vol. 21, No. 7.

Ho, et al., Animal Cell Bioreactors, Animal Cell Bioreactors, 1991, 1-512, Hardcover, Butterworth-Heinemann.

Hoehn, et al., Morphological and Biochemical Heterogeneity of Amniotic Fluid Cells in Culture, Methods in Cell Biology, 1982, pp. 11-34, vol. 26, Academic Press, Inc.

Hoffman, et al., Characterization and Culture of Human Embryonic Stem Cells, Nature Biotechnology, 2005, pp. 699-708, vol. 23, No. 6.

Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.

Hosoya, et al., Induction of Differentiation of Undifferentiated Cells into Pancreatic Beta-Cells in Vertebrates, Int. J. Dev. Biol., 2012, pp. 313-323, vol. 56.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Jaenisch, et al., Stem Cells, the Molecular Circuitry of Pluripotency and Nuclear Reprogramming, cell, Feb. 22, 2008, pp. 567-582, vol. 132, Elsevier Inc.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Jiang, et al., In Vitro Derivation of Functional Insulin-Producing Cells from Human Embryonic Stem Cells, Cell Research, 2007, pp. 333-344, vol. 17.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Karvonen, et al., Incidene of Childhood Type 1 Diabetes Worldwide, Diabetes Care, 2000, pp. 1516-1526, vol. 23, No. 10.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

(56) References Cited

OTHER PUBLICATIONS

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Klajnert, et al., Fluorescence studies on PAMAM dendrimers interactions with bovine serum albumin, Bioelectrochemistry, 2002, pp. 33-35, vol. 55.
Kleinman et al., Basement Membrane Complexes with Biological Activity, Biochemistry, 1986, 312-318, 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova_et_al_2007, EphA-Ephrin-A-Mediated Beta Cell Communication Regulates Insulin Secretion from Pancreatic Islets, Cell, Apr. 20, 2007, pp. 359-370, vol. 129.
Koyangi et al., Inhibitio nof the Rho/ROCK Pathway Reduces Apoptosis During Transplantatation of Embryonic Stem Cell-Derived Neural Precursors, Journal of Neuroscience Research, Sep. 7, 2007, 270-280, 86, Wiley-Liss, Inc.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Ku et al., Committing Embryonic Stem Cells to Early Endocrine Pancreas In Vitro, Stem Cells, 2004, 1205-1217, 22, AlphaMed Press.
Kubo et al., Development of definitive endoderm from embryonic stem cells in culture, Development, 2004, 1651-1662, 131, The Company of Biologists.
Kubota,et al., Growth factors essential for self-renewal and expansion of mouse spermatogonial stem cells, cell Biology, Nov. 23, 2004, pp. 16489-16494, vol. 101 , Issue 47.
Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Lanza, et al., Characteristics and Characterization of Human Pluripotent Stem Cells, Stem Cell Anthology, 2010, pp. 141, 142, 144 and 146, 1st Edition.
Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.
Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.
Larsen, et al., Use of the Gootingen Minipig as a Model of Diabetes, with Special Focus on Type 1 Diabetes Research, ILAR Journal, 2004, pp. 303-313, vol. 45, No. 3.
Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.
Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.
Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.
Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.
Lee, et al., PKC—Inhibitors Sustain Self-Renewal of Mouse Embryonic Stem Cells Under Hypoxia in Vitro, Experimental and Molecular Medicine, Apr. 2010, pp. 294-301, vol. 43, No. 4.
Lee, et al., Protein Kinase A- and C-Induced Insulin Release from Ca2+-Insensitive Pools, Cellular Signalling, 2003, pp. 529-537, vol. 15.
Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.
Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.
Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.
Levenstein et al., Basic Fibroblast Growth Factor Support of Human Embryonic Stem Cell Self-Renewal, Stem Cells, Nov. 10, 2005, 568-574, 24, AlphaMed Press.
Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Li, et al., Pluripotency Can be Rapidly and Efficiently Induced in Human Amniotic Fluid-Derived Cells, Human Molecular Genetics, 2009, pp. 4340-4349, vol. 18, No. 22.
Lilja et al., Cyclin-dependent Kinase 5 Promotes Insulin Exocytosis, Journal of Biological Chemistry, Jul. 6, 2001, 34199-34205, 36-7, JBC Papers in Press.
Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Loh, et al., Genomic Approaches to Deconstruct Puripotency, Annu Rev Genomics Hum Genet, 2011, pp. 165-185, vol. 12.
Ludwig, et al., Defined Culture Media for Human Embryonic Stem Cells, Embryonic Stem Cells, 2007, pp. 1-16, XP009185398, Springer.
Ludwig, et al., Derivation of Human Embryonic Stem Cells in Defined Conditions, Nature Biotechnology, Feb. 2006, pp. 185-187, vol. 24 No. 2.

(56) References Cited

OTHER PUBLICATIONS

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro- and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

McKiernan, et al., Directed Differentiation of Mouse Embryonic Stem Cells into Pancreatic-Like or Neuronal- and Glial-Like Phenotypes, Tissue Engineering, 2007, pp. 2419-2430, vol. 13, No. 10.

McLean, et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Micallef et al., Retinoic Acid Induces Pdx1-Positive Endoderm in Differentiating Mouse Embryonic Stem Cells, Diabetes, Feb. 2005, 301-305, 54, American Diabetes Association.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.

Mitalipova, et al., Preserving the Genetic Integrity of Human Embyonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem Cells, Stem Cells, 2004, 433-440, 22, AlphaMed Press.

Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

Muchamuel, et al., Preclinical Pharmacology and in Vitro Characterization of PR-047, an Oral Inhibitor of the 20s Proteasome, Blood, Nov. 16, 2008, p. 1257, vol. 112, No. 11.

Munoz, et al., Conventional Pluripotency Markers are Unspecific for Bovine Embryonic-Derived Cell-Lines, Theriogenology, 2008, pp. 1159-1164, vol. 69.

Murtha, et al., Evaluation of a Novel Technique for Wound Closure Using a Barbed Suture, Cosmetic, Aug. 2, 2005, pp. 1769-1780, vol. 117, No. 6.

Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.

Nakamura, et al., Ocular Surface Reconstruction Using Cultivated Mucosal Epithelial Stem Cells, Cornea, Oct. 2003, S75-S80, vol. 22, Supplement 1.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Nicholas et al., A Method for Single-Cell Sorting and Expansion of Genetically modified Human Embryonic Stem Cells, Stem Cells and Development, 2007, 109-117, 16, Mary Ann Liebert, Inc.

Nie, et al., Scalable Passaging of Adherent Human Pluripotent Stem Cells, PLOS One, 2014, pp. 1-9, vol. 9, Issue 1.

Nishimura, et al., Expression of MafA in Pancreatic Progenitors is Detrimental for Pancreatic Development, Developmental Biology, 2009, pp. 108-120, vol. 333.

Nostro, et al., Generation of Beta Cells from Human Pluripotent Stem Cells: Potential for Regenerative Medicine, Seminars in Cell & Developmental Biology, 2012, pp. 701-710, vol. 23.

Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.

Odom, et al., Control of Pancreas and Liver Gene Expression by HNF Transcription Factors, Science, 2004, pp. 1378-1381, vol. 303, No. 5662.

Oh, et al., Human Embryonic Stem Cells: Technological Challenges Towards Therapy, Clinical and Experimental Pharmacology and Physiology, 2006, pp. 489-495, vol. 33.

Okita, et al., Generation of Germline-Competent Induced Pluripotent Stem Cells, Nature, Jul. 19, 2007, pp. 313-317, vol. 448.

(56) References Cited

OTHER PUBLICATIONS

Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Ouziel-Yahalom, et al., Expansion and Redifferentiation of Adult Human Pancreatic islet Cells, Biochemical and Biophysical Research Communications, 2006, pp. 291-298, vol. 341.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Park, et al., Effects of Activin A on Pancreatic Ductal Cells in Streptozotocin-Inducted Diabetic Rats, Experimental Transplantation, 2007, pp. 925-930, vol. 83.
Peerani, et al., Niche-Mediated Control of Human Embryonic Stem Cell Self-Renewal and Differentiation, The EMBO Journal, 2007, pp. 4744-4755, vol. 26.
Perrier, et al., Derivation of Midbrain Dopamine Neurons from Human Embryonic Stem Cells, PNAS, Aug. 24, 2004, pp. 12543-12548, vol. 101, No. 34.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578 XP009090586, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct. 4—Expressing Cells in Human Amniotic Fluid: a New Source for Stem Cell Research?, Human Reproduction, 2003, pp. 1489-1493, vol. 18, No. 7.
Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, Embryonic & Induced Pluripotent Stem Cell Transcription Factors, 2013, http://www.rndsystems.com/molecule_group.aspx?r=1&g-3041, 2 page web printout.
R&D Systems, Pancreatic Endoderm, Pancreatic Endoderm, Jun. 24, 2013, http://www.rndsystems.com/molecule_group.aspx?g=801&r, 1 page web printout.
Rajagopal, et al., Insulin Staining of ES Cell Progeny from Insulin Uptake, Science, Jan. 17, 2003, pp. 363, vol. 299.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-281, vol. 6.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34 , Issue 4.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania, et al., Enrichman of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richards, et al., Development of Defined Media for the Serum-Free Expansion of Primary Keratinocytes and Human Embryonic Stem Cells, Tissue Engineering, 2008, pp. 221-232, vol. 14, No. 3.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ross, et al., Cytochrome P450s in the Regulation of Cellular Retinoic Acid Metabolism, Annu. Rev. Nutr., 2011, pp. 65-87, vol. 31.
Rowley, et al., Meeting Lot-Size Challenges of Manufacturing Adherent Cells for Therapy, Cell Therapies Manufacturing, 2012, pp. 16-22, vol. 10, No. 3.
Ryan, et al., Clinical Outcomes and Insulin Secretion After Islet Transplantation with the Edmonton Protocol, Diabetes, Apr. 2001, pp. 710-719, vol. 50.

(56) References Cited

OTHER PUBLICATIONS

Sakaguchi, et al., Integration of Adultmesenchymal Stem Cells in the CNS, Society for Neuroscience Abstract Viewer and Itineray Planner, 2002, XP002519394, Program 237.18.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.

Sato, et al., Manipulation of Self-Renewal in Human Embryonic Stem Cells Through a Novel Pharmacological GSK-3 Inhibitor, Methods in Molecular Biology, 2006, pp. 115-128, vol. 331.

Sato, et al., Molecular Signature of Human Embryonic Stem Cells and its Comparison with the Mouse, Developmental Biology, Apr. 23, 2003, pp. 404-413, vol. 260.

Savino et al., Generation of Interleukin-6 Receptor Antagonists by Molecular-Modeling Guided Mutagenesis of Residues Important for gp130 Activation, EMBO Journal, 1994, 1357-1367, 13-6, IT.

Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182 , Issue 2.

Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Schraermeyer, et al., Subretinally Transplanted Embryonic Stem Cells Rescue Photoreceptor Cells From Degeneration in the RCS Rats, Cell Transplantation, 2001, pp. 673-680, vol. 10.

Schroeder, et al., Differentiation of Mouse Embryonic Stem Cells to Insulin-Producing Cells, Nature Protocols, 2005, pp. 495-507, vol. 1, No. 2.

Schuldiner, et al., Induced Neuronal Differentiation of Human Embryonic Stem Cells, Brain Research, 2001, pp. 201-205, vol. 913.

Schulz, et al., A Scalable System for Production of Functional Pancreatic Progenitors from Human Embryonic Stem Cells, PLOS One, 2012, pp. 1-17, vol. 7, Issue 5.

Scullica, et al., Diagnosis and Classification of Macular Degenerations: an Approach Based on Retinal Function Testing, Documenta Ophthalmologica, 2001, pp. 237-250, vol. 102.

Seaberg et al., Cfonal identification of multipotent precursors from adult~mouse pancreas that generate neural and pancreatic lineages, Nature Biotechnology, Sep. 2004, pp. 1115-1124, vol. 22, No. 9, Nature Publishing Group.

Segev, et al., Differentiation of Human Embryonic Stem Cells into Insulin-Producing Clusters, Stem Cells, Jan. 1, 2004, pp. 265-274.

Serafimidis, et al., Novel Effectors of Directed and Ngn3-Mediated Differentiation of Mouse Embryonic Stem Cells Into Endocrine Pancreas Progenitors, Stem Cells, 2008, pp. 3-16, vol. 26.

Shackleton, et al., Generation of a Functional Mammary Gland from a Single Stem Cell, Nature, Jan. 5, 2006, pp. 84-88, XP002567665, vol. 439.

Shamblott et al., Derivation of pluripotent stem cells from cultured human primordial germ cells, Developmental Biology, Nov. 1998, 13726-13731, 95, National Academy of Sciences.

Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.

Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.

Shim, et al., Directed Differentiation of Human Embryonic Stem Cells Towards a Pancreatic Cell Fate, Diabetologia, 2007, pp. 1228-1238, vol. 50.

Shindler et al., A synthetic nanofibrillar matrix promotes in vivo-like organization and morphogenesis for cells in culture, Biomaterials, Apr. 18, 2005, 5624-5631, 26, Elsevier.

Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.

Shiraki, et al., Guided Differentiation of Embryonic Stem Cells into Pdx1-Expressing Regional-Specific Definitive Endoderm, Stem Cells, 2008, pp. 874-885, vol. 26.

Sidhu et al., Derivation of Three Clones from Human Embryonic Stem Cell Lines by FACS Sorting and Their Characterization, Stem Cells and Development, 2006, 61-69, 15, Mary Ann Liebert, Inc.

Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.

Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.

Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.

Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.

Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.

Sneddon, et al., Self-Renewal of Embryonic-Stem-Cell-Derived Progenitors by Organ-Matched Mesenchyme, Nature, Nov. 29, 2012, pp. 765-770, vol. 491.

Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.

Soria, et al., From Stem Cells to Beta Cells: New Strategies in Cell Therapy of Diabetes Mellitus, Diabetologia, 2001, pp. 407-415, vol. 44.

Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.

Spence, et al., Translation Embryology: Using Embryonic Principles to Generate Pancreatic Endocrine Cells from Embryonic Stem Cells, Developmental Dynamics, 2007, pp. 3218-3227, vol. 236.

Stacpoole, et al., Efficient Derivation of Neural Precuros Cells, Spinal Motor Neurons and Midbr, Nat Protoc, 2012, pp. 1-26, vol. 6, Issue 8.

Stadtfeld, et al., Defining Molecular Cornerstones During Fibroblast to iPS Cell Reprogramming in Mouse, Cell Stem Cell, Mar. 2008, pp. 230-240, vol. 2.

Stafford, et al., Retinoic Acid Signaling is Required for a Critical Early Step in Zebrafish Pancreatic Development, Current Biology, 2002, pp. 1215-1220, vol. 12, Issue 14.

Stafford, et al., Retinoids Signal Directly to Zebrafish Endoderm to Specify Insuilin-Expressing B-cells, Development, 2005, pp. 949-956, vol. 133.

(56) References Cited

OTHER PUBLICATIONS

Stoffel, et al., Navigating the Pathway from Embryonic Stem Cells to Beta Cells, Seminars in Cell & Developmental Biology, 2004, pp. 327-336, vol. 15.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1- and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Current Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Totonchi, et al., Feeder- and Serum-Free Establishment and Expansion of Human Induced Pluripotent Stem Cells, Int. J. Dev. Biol., 2010, pp. 8770886, vol. 54.

Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tsuchida, et al., Activin Isoforms Signal Through Type I Receptor Serine/Threonin Kinase ALK7, Molecular and Cellular Endocrinology, 2004, pp. 59-65, vol. 22.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wachs, et al., High Efficacy of Clonal Growth and Expansion of Adult Neural Stem Cells, Laboratory Investigation, 2003, pp. 949-962, vol. 83, No. 7.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.

(56) References Cited

OTHER PUBLICATIONS

Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9. XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.

Yang, et al., Evaluation of Humam MSCs Cell Cycle, Viability and Differentiation in Micromass Culture, Biorheology, 2006, p. 489-496, vol. 43 (English Abstract Only).
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zalzman, et al., Differentiation of Human Liver-Derived, Insulin-Producing Cells Toward the B-Cell Phenotype, Diabetes, 2005, pp. 2568-2575, vol. 54.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun. 2005, 4969-4976, 25-12, American Society for MIcrobiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.
Zhang et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Zuscik, et al., Regulation of Chondrogenesis and Chondrocyte Differentiation by Stress, J Clin Invest, 2008, pp. 429-438, vol. 118, Issue 2.

* cited by examiner

IH-3

IH-1

IH-6

TeSR®1

IH-3

IH-3

TeSR®1

IH-3

IH-1

TeSR®1

ZFP42

SOX2

POU5F1

NANOG

FOXA2

AFP

KI67

OCT4

SOX17

FOXA2

SOX2

OCT4

FOXA2

DAPI

SOX2

FOXA2

DAPI

Tesr1

IH-3

IH-3-1

IH-3-2

IH-3-3

IH-3-4

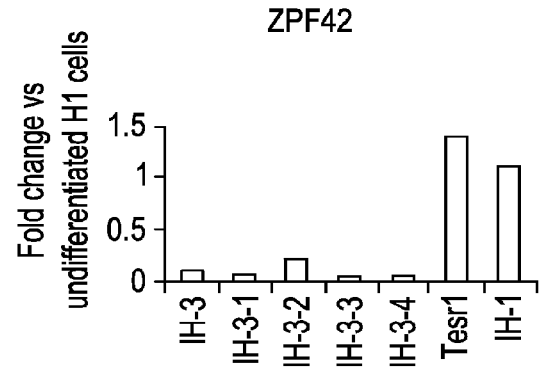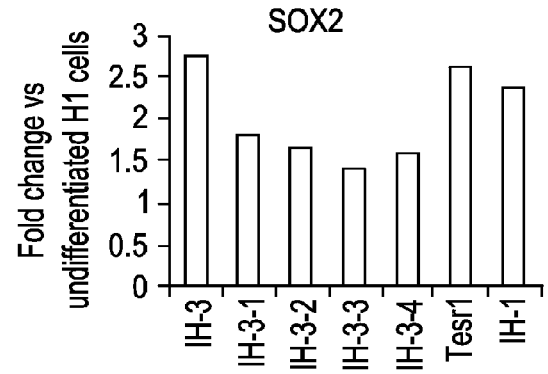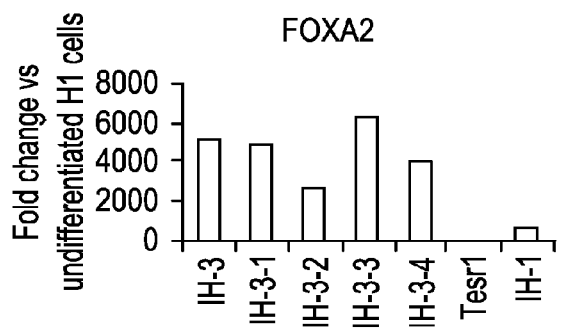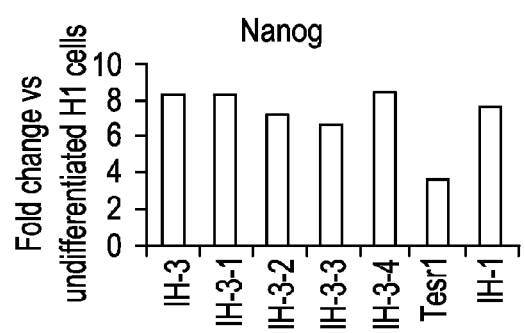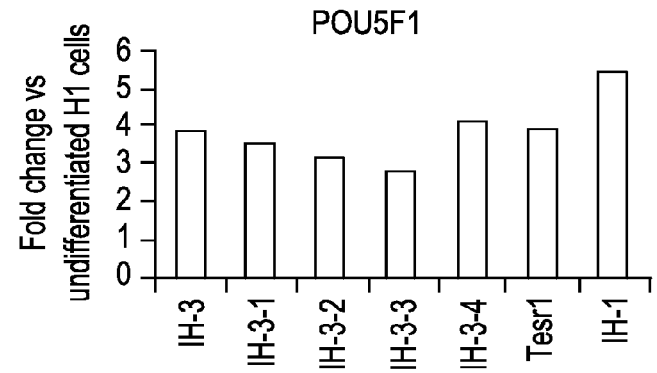

Tesr1

IH-3

IH-1

IH-3RT

AFP

FOXA2

SOX2

NANOG

POU5F1

ZFP42

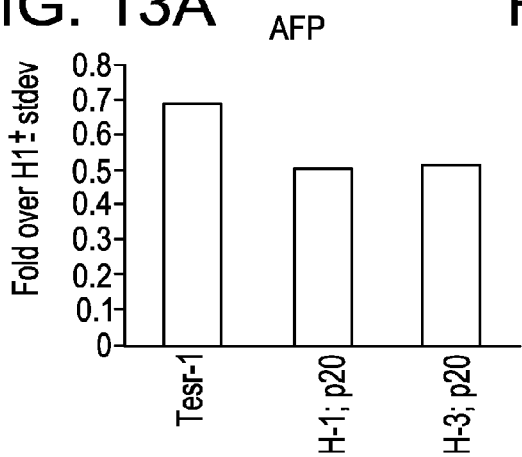
FIG. 13A  AFP
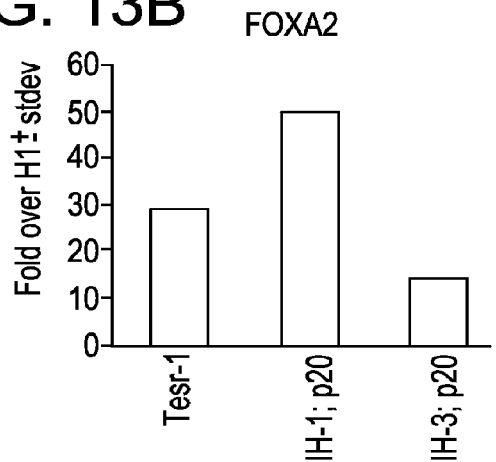
FIG. 13B  FOXA2
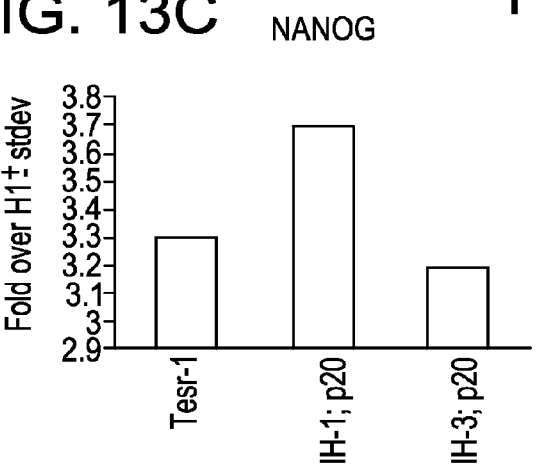
FIG. 13C  NANOG
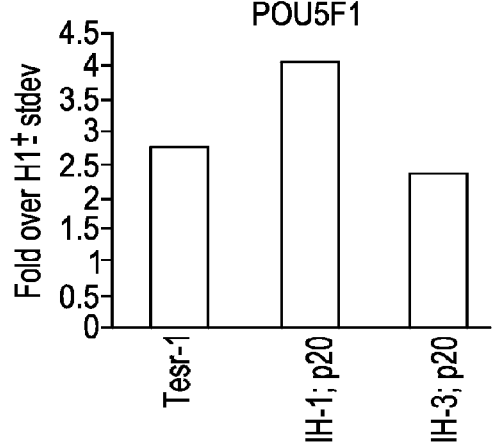
FIG. 13D  POU5F1
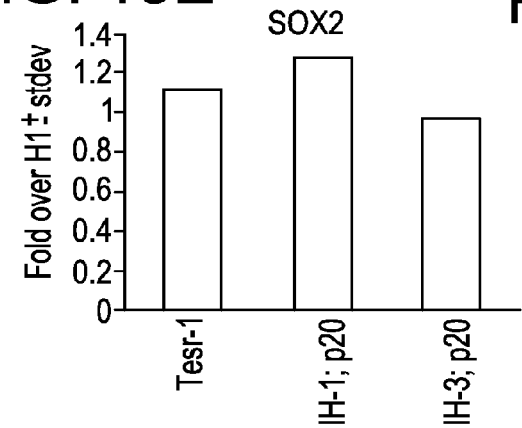
FIG. 13E  SOX2
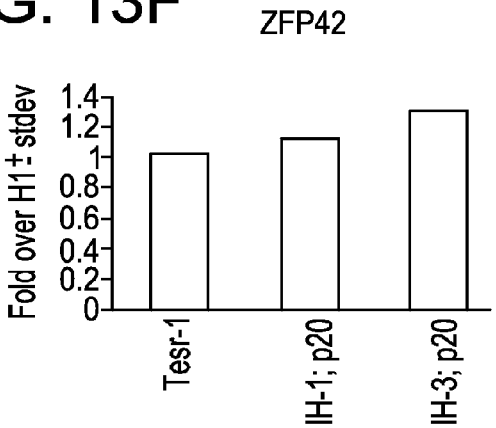
FIG. 13F  ZFP42

Sigma BSA – P0

Fatty-acid free BSA – P0

Sigma BSA – P3

Fatty-acid free BSA – P3

AFP

MIXL1

T

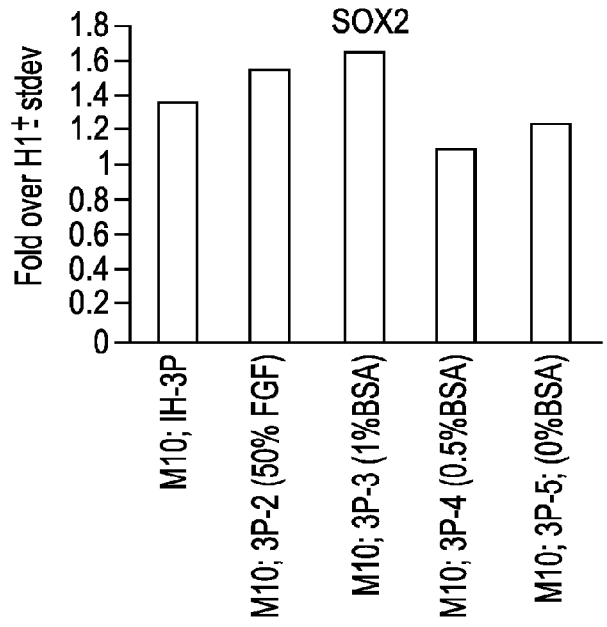
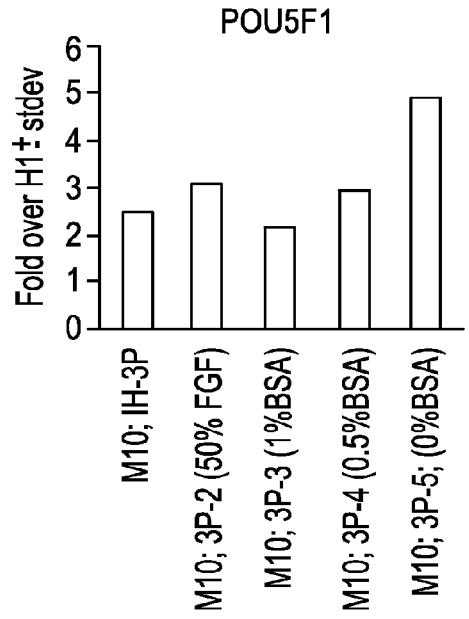
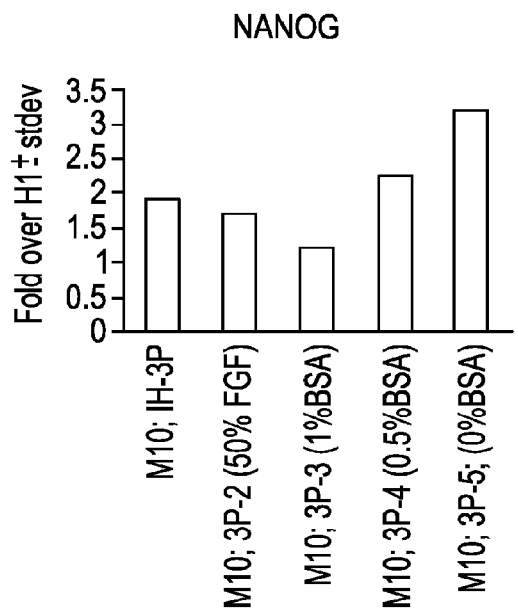
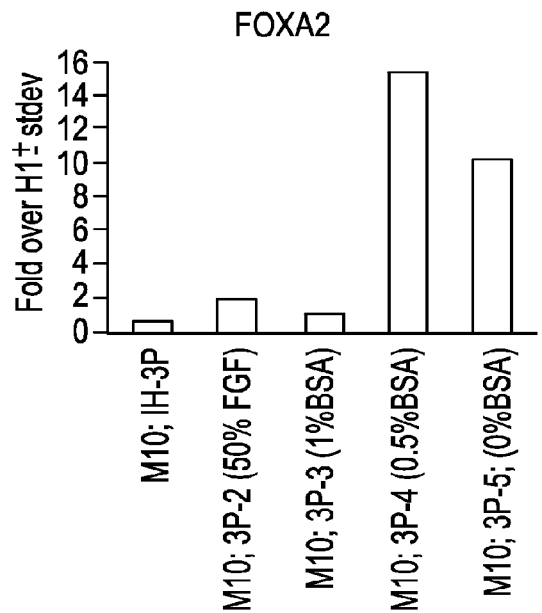

IH-3

IH-3P-2

IH-3P-3

IH-3P-4

IH-3P-5

DEFINED MEDIA FOR EXPANSION AND MAINTENANCE OF PLURIPOTENT STEM CELLS

CROSS REFERENCE TO RELATED APPLICATION

The present application is a divisional application of U.S. patent application Ser. No. 13/787,173, filed Mar. 6, 2013 (now U.S. Pat. No. 9,434,920, issued Sep. 6, 2016), which claims the benefit of U.S. Provisional Patent Application Ser. No. 61/607,706, filed Mar. 7, 2012, both of which are incorporated herein by reference in their entirety for all purpose.

FIELD OF THE INVENTION

The present invention is in the field of proliferation and maintenance of pluripotent stem cells under defined media conditions.

BACKGROUND

Expansion of undifferentiated pluripotent stem cells has been traditionally employed "feeder" cells which provide sufficient factors to support attachment, proliferation and maintenance of pluripotency markers. Early methods for the generation and culture of human embryonic stem cells required the use of mouse embryonic fibroblast (MEF) feeder cells. Subsequent techniques included use of "conditioned media" and an extracellular matrix coating to replace feeder cells. Conditioned media is media that has been modified by feeder cells, such as MEFs. However, both methods suffer from inconsistencies in batches of conditioned media or feeder cells to continually support expansion of pluripotent stem cells. Furthermore, both systems provide undefined factors that may work differently on different pluripotent stem cells. Accordingly, establishing a defined, cheap, reproducible culture media that supports continual expansion of pluripotent stem cells is of great interest in the regenerative medicine field.

A defining feature of human embryonic stem cells (hES cells) is that the cells have a tendency to differentiate into various lineages. This unwanted differentiation can hamper uniform and directed differentiation required to subsequently generate desired specific cell types. In fact, both feeder cells and conditioned media culture conditions typically result in some level of unwanted differentiation, particularly around the edges of the growing ES cell colony or in the center of the colony.

Recent efforts have resulted in replacement of feeder cells or conditioned media with a host of replacement culture conditions, such as knock-out serum replacer (KSR) in the media (Chen et al., 2005, Nature Methods, 2:185-189). KSR contains a crude undefined fraction of bovine serum albumin (BSA). Others have shown long-term maintenance of pluripotency in a chemically defined media with FGF2, activin A, and insulin (Vallier et al., 2005, J Cell Sci, 118:4495-4509) Commercially available media formulations including mTeSR®1 media (StemCell Technologies, Vancouver, Canada) and StemPro™ (Invitrogen, CA) have also been previously used to maintain and proliferate human pluripotent stem cells. Additional prior art focusing on development of defined media include U.S. Pat. No. 7,449,334, U.S. Pat. No. 7,442,548, U.S. Pat. No. 7,005,252, US2008/0268534, U.S. Pat. No. 7,410,798, U.S. Pat. No. 7,297,539, and U.S. Pat. No. 6,800,480. Furthermore, a recent publication further refined the mTeSR®1 media to eight components (Nature Methods, 2011, 8:424-429) highlighting that even in defined media there exists unnecessary agent(s) that may actually slow the proliferation of ES cells or reduce their pluripotency state. The refined mTeSR®1 media consists of DMEM/F12 basal media supplemented with insulin, selenium, transferrin, ascorbic acid, FGF2 (bFGF), and TGFβ or nodal, having the pH adjusted with NaHCO$_3$.

It is therefore clear that there is still a need for fully defined media conditions that provide consistency regarding expansion of pluripotent cells while having minimal number of added components.

SUMMARY

The present invention provides a defined cell culture formulation for the culture, maintenance, and expansion of pluripotent stem cells, wherein the defined cell culture formulation comprises basal medium, insulin, transferrin, selenium, fatty-acid free albumin, a TGF-β ligand, bFGF, and ascorbic acid; and wherein culturing stem cells in the defined cell culture formulation maintains the pluripotency and karyotypic stability of the stem cells for at least 10 passages. In some embodiments of the invention, the cell culture formulation further comprises insulin growth factor 1 (IGF-1). In some embodiments of the invention, the cell culture formulation comprises DMEM-F12.

The invention provides a defined cell culture formulation for the culture, maintenance, and expansion of pluripotent stem cells, wherein the defined cell culture formulation comprises basal medium, insulin, transferrin, selenium, fatty-acid free albumin, a TGF-β ligand, bFGF, ascorbic acid, TRACE ELEMENTS C (1.20 mg/L AlCl$_3$.6H$_2$O, 0.17 mg/L AgNO$_3$, 2.55 mg/L Ba(C$_2$H$_3$O$_2$)$_2$, 0.12 mg/L KBr, 2.28 mg/L CdCl$_2$, 2.38 mg/L CoCl$_2$.6H$_2$O, 0.32 mg/L CrCl$_3$ (anhydrous), 4.20 mg/L NaF, 0.53 mg/L GeO$_2$, 0.17 mg/L KI, 1.21 mg/L RbCl, and 3.22 mg/L ZrOCl$_2$.8H$_2$O), 4-(2-hydroxyethyl)-1-piperazine-ethanesulfonic acid, lithium chloride, glucose, GIBCO® CHEMICALLY DEFINED LIPID CONCENTRATE ("DEFINED LIPIDS") (Life Technology Corporation) (100.0 ml/L ethyl alcohol (200 proof) and 2 mg/L Arachidonic Acid, 220 mg/L Cholesterol, 70 mg/L DL-alpha-Tocopherol Acetate, 0 mg/L Ethyl Alcohol 100%, 10 mg/L Linoleic Acid, 10 mg/L Linolenic Acid, 10 mg/L Myristic Acid, 10 mg/L Oleic Acid, 10 mg/L Palmitic Acid, 10 mg/L Palmitoleic Acid, 90000 mg/L Pluronic F-68, 10 mg/L Stearic Acid, and 2200 mg/L Tween 80® (polysorbate 80 sold under the trade name TWEEN 80 by ICI Americas, Inc. Bridgewater, N.J.)), and L-alanyl-L-glutamine dipeptide; and wherein culturing stem cells in the defined cell culture formulation maintains the pluripotency and karyotypic stability of the stem cells for at least 10 passages. In some embodiments of the invention, the cell culture formulation comprises MCDB-131.

In some embodiments of the invention, GIBCO® Insulin-Transferrin-Selenium-X (a basal medium supplement containing insulin (1.00 g/L), transferrin (0.55 g/L), selenium (sodium selenite 0.00067 g/L) and ethanolamine (0.20 g/L)) ("ITS-X") (Life Technologies Corporation, Carlsbad, Calif.) provides the insulin, transferrin, and selenium for the defined cell culture formulation of the invention. In some embodiments of the invention, the ITS-X is present from about 0.5% to about 2%. In some embodiments of the invention, the ITS-X is present at about 1%. In some embodiments of the invention, the fatty acid free albumin is reagent grade. In some embodiments of the invention, the reagent grade fatty acid-free BSA is present from about 0.2% to about 2.5%. In some embodiments of the invention, the reagent grade fatty acid-free BSA is present at about 2%.

In some embodiments, the TGF-β ligand in the defined cell culture formulation of the invention is TGF-β1. In some embodiments of the invention, the TGF-β1 is present from about 0.5 ng/ml to about 10 ng/ml. In some embodiments of the invention, the TGF-B1 is present at about 1 ng/ml.

In some embodiments of the invention, the bFGF is present in the cell culture formulation from about 50 ng/ml to about 100 ng/ml. In some embodiments of the invention, the bFGF is present in the defined cell culture formulation at about 50 ng/ml. In some embodiments, the bFGF is present in the defined cell culture formulation at about 100 ng/ml.

In some embodiments of the invention, the insulin growth factor 1 (IGF-1) is present from about 10 ng/ml to about 50 ng/ml. In some embodiments of the invention, the IGF-1 is present in the defined cell culture formulation at about 20 ng/ml.

In some aspects of the invention, ascorbic acid is present in the defined cell culture formulation from about 0.2 mM to about 0.3 mM. In some aspects of the invention, ascorbic acid is present in the defined cell culture formulation at about 0.25 mM.

In an embodiment, the invention concerns a defined cell culture formulation consisting essentially of DMEM-F12 basal medium, ITS-X (insulin (1.00 g/L), transferrin (0.55 g/L), selenium (sodium selenite 0.00067 g/L) and ethanolamine (0.20 g/L)) (Life Technologies Corporation, Carlsbad, Calif.) (to provide insulin, transferrin, and selenium), fatty-acid free albumin, a TGF-β ligand, bFGF, insulin growth factor 1 (IGF-1), and ascorbic acid.

In an embodiment, the invention relates to a defined cell culture formulation consisting essentially of MCDB-131, (insulin (1.00 g/L), transferrin (0.55 g/L), selenium (sodium selenite 0.00067 g/L) and ethanolamine (0.20 g/L)) (Life Technologies Corporation, Carlsbad, Calif.), fatty-acid free albumin, a TGF-β ligand, bFGF, ascorbic acid, TRACE ELEMENTS C (1.20 mg/L AlCl$_3$.6H$_2$O, 0.17 mg/L AgNO$_3$, 2.55 mg/L Ba(C$_2$H$_3$O$_2$)$_2$, 0.12 mg/L KBr, 2.28 mg/L CdCl$_2$, 2.38 mg/L CoCl$_2$.6H$_2$O, 0.32 mg/L CrCl$_3$ (anhydrous), 4.20 mg/L NaF, 0.53 mg/L GeO$_2$, 0.17 mg/L KI, 1.21 mg/L RbCl, and 3.22 mg/L ZrOCl$_2$.8H$_2$O), 4-(2-hydroxyethyl)-1-piperazine-ethanesulfonic acid, lithium chloride, glucose, GIBCO® CHEMICALLY DEFINED LIPID CONCENTRATE (Life Technology Corporation) (100.0 ml/L ethyl alcohol (200 proof) and 2 mg/L Arachidonic Acid, 220 mg/L Cholesterol, 70 mg/L DL-alpha-Tocopherol Acetate, 0 mg/L Ethyl Alcohol 100%, 10 mg/L Linoleic Acid, 10 mg/L Linolenic Acid, 10 mg/L Myristic Acid, 10 mg/L Oleic Acid, 10 mg/L Palmitic Acid, 10 mg/L Palmitoleic Acid, 90000 mg/L Pluronic F-68, 10 mg/L Stearic Acid, and 2200 mg/L Tween 80® (polysorbate 80 sold under the trade name TWEEN 80 by ICI Americas, Inc. Bridgewater, N.J.)), and L-alanyl-L-glutamine dipeptide.

In an embodiment, the invention concerns a method for the expansion of human pluripotent stem cells, where the method comprises culturing the human pluripotent stem cells on a feeder-free matrix in a defined cell culture formulation; where the defined cell culture formulation comprises basal medium, insulin, transferrin, selenium, fatty-acid free albumin, a TGF-β ligand, bFGF, and ascorbic acid; and where culturing the stem cells in the defined cell culture formulation maintains the pluripotency and karyotypic stability of the cells for at least 10 passages. In some embodiments, the defined cell culture formulation further comprises insulin growth factor 1 (IGF-1). In some embodiments, the cell culture formulation comprises DMEM-F12.

In an embodiment, the invention relates to a method for the expansion of human pluripotent stem cells, where the method comprises culturing the human pluripotent stem cells on a feeder-free matrix in a defined cell culture formulation; where the defined cell culture formulation comprises basal medium, insulin, transferrin, selenium, fatty-acid free albumin, a TGF-β ligand, bFGF, ascorbic acid, IGF-1, TRACE ELEMENTS C (1.20 mg/L AlCl$_3$.6H$_2$O, 0.17 mg/L AgNO$_3$, 2.55 mg/L Ba(C$_2$H$_3$O$_2$)$_2$, 0.12 mg/L KBr, 2.28 mg/L CdCl$_2$, 2.38 mg/L CoCl$_2$.6H$_2$O, 0.32 mg/L CrCl$_3$ (anhydrous), 4.20 mg/L NaF, 0.53 mg/L GeO$_2$, 0.17 mg/L KI, 1.21 mg/L RbCl, and 3.22 mg/L ZrOCl$_2$.8H$_2$O), 4-(2-hydroxyethyl)-1-piperazineethanesulfonic acid, lithium chloride, glucose, GIBCO® CHEMICALLY DEFINED LIPID CONCENTRATE (Life Technology Corporation) (100.0 ml/L ethyl alcohol (200 proof) and 2 mg/L Arachidonic Acid, 220 mg/L Cholesterol, 70 mg/L DL-alpha-Tocopherol Acetate, 0 mg/L Ethyl Alcohol 100%, 10 mg/L Linoleic Acid, 10 mg/L Linolenic Acid, 10 mg/L Myristic Acid, 10 mg/L Oleic Acid, 10 mg/L Palmitic Acid, 10 mg/L Palmitoleic Acid, 90000 mg/L Pluronic F-68, 10 mg/L Stearic Acid, and 2200 mg/L Tween 80® (polysorbate 80 sold under the trade name TWEEN 80 by ICI Americas, Inc. Bridgewater, N.J.)), and L-alanyl-L-glutamine dipeptide. In some embodiments, the cell culture formulation used in the method for the expansion of human pluripotent stem cells, comprises MCDB-131.

An embodiment of the present invention is an in vitro cell population wherein greater than 50% of the cell population is positive for protein expression of OCT4, SOX2, NANOG, and FOXA2 with negative or low protein expression of SSEA-4 and ZFP42. The population is obtained by culturing pluripotent stem cells in a defined cell culture formulation comprising basal media supplemented with IGF-1, insulin, bFGF, TGF-B ligand, and fatty-acid free albumin; and where the defined cell culture formulation does not comprise ascorbic acid.

In some embodiments of the invention, the defined cell culture formulation comprises DMEM/F12 basal media. In some embodiments of the invention the cell culture formulation comprises insulin as ITS-X (insulin (1.00 g/L), transferrin (0.55 g/L), selenium (sodium selenite 0.00067 g/L) and ethanolamine (0.20 g/L)) (Life Technologies Corporation, Carlsbad, Calif.). In some embodiments of the invention, the ITS-X is present from about 0.5% to about 2%. In some aspects of the invention, the ITS-X is present at about 1%. In some embodiments of the invention, the fatty acid free albumin is reagent grade. In some aspects of the invention, the reagent grade fatty acid-free albumin is present from about 0.2% to about 2.5%. In some embodiments of the invention, the reagent grade fatty acid-free albumin is present at about 2%. In some aspects of the invention, the TGF-B ligand is TGF-B1. In some embodiments of the invention, the TGF-B1 is present from about 0.5 ng/ml to about 10 ng/ml. In some aspects of the invention, the TGF-B1 is present at about 1 ng/ml.

BRIEF DESCRIPTION OF THE DRAWINGS

FIG. 10A to FIG. 10E show data from real-time PCR analyses of the expression of the following genes in cells of the human embryonic stem cell line H1 cultured in media described in Example 2 and harvested at Passage 5: ZFP42 (FIG. 10A), SOX2 (FIG. 10B), FOXA2 (FIG. 10C), Nanog (FIG. 10D), and POU5F1 (OCT4) (FIG. 10E).

FIG. 13A to FIG. 13F show data from real-time PCR analyses of the expression of the following genes in cells of the human embryonic stem cell line H1 cultured for 20 passages in mTeSR®1 media, and IH-1 and IH-3 media described in Example 3: AFP FIG. 13A), FOXA2 (FIG. 13B), Nanog (FIG. 13C), POU5F1 (OCT4) (FIG. 13D), SOX2 (FIG. 13E), and ZFP42 (FIG. 13F).

FIG. 17A to FIG. 17D show data from real-time PCR analyses of the expression of the following genes in cells of the human embryonic stem cell line H1 cultured for ten passages in media formulations described in Example 6: SOX2 (FIG. 17A), POU5F1 (FIG. 17B), Nanog (FIG. 17C), and FOXA2 (FIG. 17C).

DETAILED DESCRIPTION

Figure 1A:
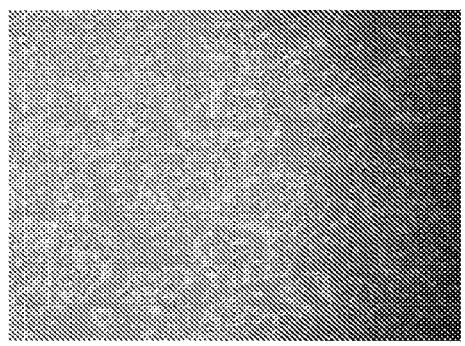
FIG. 1A to FIG. 1D show phase-contrast images of H1 cells cultured for 3 passages in IH-3 (FIG. 1A), IH-1 (FIG. 1B), IH-6 (FIG. 1C), and mTeSR®1 (FIG. 1D).

For clarity of disclosure, and not by way of limitation, the detailed description of the invention is divided into the following subsections that describe or illustrate certain features, embodiments or applications of the present invention.

DEFINITIONS

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extra-embryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers," as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Basal Medium" refers to a solution of salts, nutrients, and vitamins that can support the growth of pluripotent stem cells in culture. Basal media may be selected among others from Dulbecco's modified Eagle's media (DMEM), MCDB media, RPMI. DMEM may also be DMEM/F12 (also referred to as DM-F12), or DMEM-high glucose (also referred to as DMEM-hg). MCDB media may be selected from any of the MCDB media available, and specifically MCDB-131. Alternatively, basal media may be selected by mixing the basal media formulations listed above in the appropriate ratio to allow for proliferation and maintenance of pluripotency of embryonic stem cells. In some embodiments, the basal media in the defined cell culture formulation of the invention is DMEM-F12. In some embodiments, the basal media in the cell culture formulation of the invention is MCDB-131.

"Feeder Cells" refers to non-pluripotent stem cells on which pluripotent stem cells are plated. The feeder cells provide sufficient soluble and insoluble factors to support for attachment, proliferation, and maintenance of pluripotency markers by pluripotent stem cells.

"Conditioned Medium" refers to a medium that is further supplemented with soluble factors derived from feeder cells.

"Extracellular Matrix" or "Defined Matrix" or "Synthetic Matrix" refers to one or more substances that can provide for attachment, proliferation, and maintenance of pluripotency markers by pluripotent stem cells. Used interchangeably herein are "IGF" and "IGF-1" which stand for Insulin-like growth factor 1. In humans, this protein is made by the liver and is responsible for much of what is attributed to the human growth hormone.

As used herein, "FGF2" and "bFGF" are used interchangeably to identify the human basic fibroblast growth factor.

Used interchangeably herein are "TGF beta", "TGF-B", and "TGF-3". A TGF-β ligand may be selected from bone morphogenetic proteins (BMPs), growth and differentiation factor (GDFs), activins (Activin A, Activin AB, Activin B, Activin C), nodal and TGF-βs. A TGF-β may be selected from TGF-β1, TGF-β2, activin A, and TGF-β3.

ISOLATION, EXPANSION AND CULTURE OF PLURIPOTENT STEM CELLS

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra 1-60, and Tra1-81 expression (if present) and increased expression of SSEA-1. Undifferentiated pluripotent stem cells typically have alkaline phosphatase activity, which can be detected by fixing the cells with 4% paraformaldehyde, followed by developing with Vector® Red as a substrate, as described by the manufacturer (Vector Laboratories, Burlingame Calif.). Undifferentiated pluripotent stem cells also typically express OCT4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered. Pluripotent cells may be readily expanded in culture using various feeder layers or by using matrix protein coated vessels. Alternatively, chemically defined surfaces in combination with defined media such as mTeSR®1 media (StemCell Technologies, Vancouver, Canada) may be used for routine expansion of the cells. Pluripotent cells may be readily removed from culture plates using enzymatic, mechanical or use of various calcium chelators such as EDTA (ethylenediaminetetraacetic acid). Alternatively, pluripotent cells may be expanded in suspension in the absence of any matrix proteins or a feeder layer.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10 to 12 weeks gestation. Non-limiting examples are established lines of human embryonic stem cells or human embryonic germ cells, such as, for example the human embryonic stem cell lines H1, H7, and H9 (WiCell Research Institute, Madison, Wis.). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are inducible pluripotent cells (IPS) or reprogrammed pluripotent cells that can be derived from adult somatic cells using forced expression of a number of pluripotent related transcription factors, such as OCT4, Nanog, Sox2, KLF4, and ZFP42 (Annu Rev Genomics Hum Genet, 2011, 12:165-185).

Human embryonic stem cells may be prepared as described by Thomson et al. (U.S. Pat. No. 5,843,780; Science, 1998; 282:1145-1147; Curr Top Dev Biol, 1998; 38:133-165; 1995, Proc Natl Acad Sci USA 92:7844-7848).

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, Tra 1-60, Tra 1-81.

Differentiation markers typically present in cultures of embryonic stem cells include for example, AFP, FOXA2, SOX17, T(BRY), and MIXL1.

In an embodiment of the present invention, human pluripotent stem cells are cultured in a defined media comprising ascorbic acid, IGF, insulin, bFGF, TGF-B ligand, and fatty-acid free albumin to sustain proliferation of the pluripotent stem cells while maintaining pluripotency and karyotypic stability of the expanded cells for at least 10 passages.

An embodiment of the present invention is an in vitro cell population wherein greater than 50% of the cell population is positive for protein expression of OCT4, SOX2, NANOG, and FOXA2 positive but low protein expression of SSEA-4 and ZFP42.

Another aspect of the present invention describes an in vitro defined cell culture formulation comprising IGF, insulin, bFGF, TGF-B, fatty-acid free albumin, and no ascorbic acid that results in a cell population wherein greater than 50% of the cell population is positive by protein staining for OCT4, SOX2, NANOG, FOXA2 and low protein expression of SSEA-4 and ZFP42.

The present invention is further illustrated, but not limited, by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims. Publications cited throughout this document are hereby incorporated by reference in their entirety.

EXAMPLE 1

Testing of Various Culture Conditions to Identify Optimal Media Components for Proliferation of Undifferentiated Embryonic Stem Cells Cells of the human embryonic stem cell line H1 (at passage 35 to passage 40), cultured on MATRIGEL™ (Catalog No. 354230, 1:30 dilution; Corning Incorporated, Corning, N.Y.) coated dishes in mTeSR®1 media (Catalog No. 05850, Stem-Cell Technologies, Inc., Vancouver BC, Canada) and passaged using ethylenediaminetetraacetic acid ("EDTA"), were used as the starting population to test various media compositions. Cells were passaged as small colonies using 5-10 min EDTA (Catalog No. #170711E, Lonza Walkersville, Inc., Walkersville, Md.) treatment at room temperature. Cultures were routinely split in a ratio of 1:6 to 1:10 at each passage. Table I lists the initial media formulations tested for their ability to proliferate H1 cells while maintaining their undifferentiated morphology and pluripotency markers.

TABLE I

Media Formulations Evaluated

| Media Number | Basal Media | Added Components* |
|---|---|---|
| IH-1 | MCDB-131 (Catalog No. 10372-019, Life Technologies Corporation, Carlsbad, CA) | 1X Trace Elements C**, 0.25 mM ascorbic acid, 10 mM HEPES, 1 mM lithium chloride, 10 mM D-Glucose, 1:500 X DEFINED LIPID***, 1X ITS-X, 2% reagent grade fatty acid free BSA, 1 ng/ml TGF-B1, 100 ng/ml bFGF, 1X GlutaMAX ™ |
| IH-2 | MCDB-131 | 1X Trace Elements C**, 0.25 mM ascorbic acid, 10 mM HEPES, 1 mM lithium chloride, 10 mM D-Glucose, 1:500 X DEFINED LIPID***, 1X ITS-X, 2% lipid rich BSA, 1 ng/ml TGF-B1, 100 ng/ml bFGF, 1X GlutaMAX ™ |
| IH-3 | DMEM-F12 (Catalog No. 11330-032, Life Technologies Corporation, Carlsbad, CA) | 1X ITS-X, 2% reagent-grade fatty acid free BSA, 1 ng/ml TGF-B1, 100 ng/ml bFGF, 20 ng/ml IGF-1 |
| IH-4 | DMEM-F12 | 1X Trace Elements C**, 0.25 mM ascorbic acid, 10 mM HEPES, 1 mM lithium chloride, 10 mM D-Glucose, 1:500 X DEFINED LIPID***, 1X ITS-X, 2% BSA (New Zealand origin), 1 ng/ml TGF-B1, 100 ng/ml bFGF, 1X GlutaMAX ™ |
| IH-5 | DMEM-F12 | 1X Trace Elements C**, 0.25 mM ascorbic acid, 10 mM HEPES, 1 mM Lithium chloride, 10 mM D-Glucose, 1:500 X DEFINED LIPID***, 1X ITS-X, 2% standard grade BSA, 1 ng/ml TGF-B1, 100 ng/ml bFGF, 1X GlutaMAX ™ |
| IH-6 | DMEM-F12 | 1X Non-essential amino acids, 1X ITS-X, 20 ng/ml bFGF, 0.1 mM β-mercaptoethanol, 0.95 µM CHIR99021, |

TABLE I-continued

Media Formulations Evaluated

| Media Number | Basal Media | Added Components* |
|---|---|---|
| | | 0.4 µM PD0325901, and 10 µM Y-27632 |

*TRACE ELEMENTS C (Catalog No. #25-023-Cl, Corning Incorporated, Corning NY); HEPES (Catalog No. #15630-056-, 4-(2-hydroxyethyl)-1-piperazineethanesulfonic acid; Life Technologies Corporation, Carlsbad, CA); LiCl (Catalog No. L7026, Sigma Aldrich Co LLC, Saint Louis, MO); D-glucose (Catalog No. G8769, Sigma); ascorbic acid (Catalog No. A4403, Sigma Aldrich Co. LLC, Saint Louis, MO); DEFINED LIPID* is GIBCO ® CHEMICALLY DEFINED LIPID CONCENTRATE (Catalog No. 11905-031, Life Technologies Corporation, Carlsbad, CA); reagent-grade fatty acid free BSA (Catalog No. 7500804-, LAMPIRE Biological Laboratories, Inc., Pipersville, PA); TGF-β1 (Catalog No. 240-B-002, R & D Systems, Inc., Minneapolis, MN); bFGF (Catalog No. 233-FB-025, R & D Systems, Inc., Minneapolis, MN); IGF-1 (Catalog No. 291-G1-200, R & D Systems, Inc., Minneapolis, MN), GlutaMAX™ (Catalog No. 35050-079-, 200 mM L-alanyl-L-glutamine dipeptide in 0.85% NaCl; Life Technologies Corporation, Carlsbad, CA); Lipid rich BSA-AlbuMAX ® (Catalog No. 11021-037, Life Technologies Corporation, Carlsbad, CA); Insulin-Transferrin-Selenium-X ("ITS-X") (Catalog No. 51500-056, insulin (1.00 g/L), transferrin (0.55 g/L), selenium (sodium selenite 0.00067 g/L) and ethanolamine (0.20 g/L), Life Technologies Corporation, Carlsbad, CA); standard grade New Zealand BSA (Catalog No. 8631200, LAMPIRE Biological Laboratories, Inc., Pipersville, PA); standard grade BSA (Catalog No. 7500802, LAMPIRE Biological Laboratories, Inc., Pipersville, PA); NEAA (Catalog No. 11140-050-, Life Technologies Corporation, Carlsbad, CA); mercaptoethanol (Catalog No. 31350-010, Life Technologies Corporation, Carlsbad, CA); CHIR99021 (Catalog No. 04-0004, Stemgent, Inc., Cambridge, MA), PD0325901 (Catalog No. PZ0162, Sigma Aldrich Co LLC), Y27632 (Catalog No. Y0503, Sigma Aldrich Co LLC).
**Mediatech TRACE ELEMENTS C (previously sold by Mediatech, Inc. under Catalog No. 99-176) 1000x liquid contains: 1.20 mg/L AlCl$_3$•6H$_2$O, 0.17 mg/L AgNO$_3$, 2.55 mg/L Ba(C$_2$H$_3$O$_2$)$_2$, 0.12 mg/L KBr, 2.28 mg/L CdCl$_2$, 2.38 mg/L CoCl$_2$•6H$_2$O, 0.32 mg/L CrCl$_3$ (anhydrous), 4.20 mg/L NaF, 0.53 mg/L GeO$_2$, 0.17 mg/L KI, 1.21 mg/L RbCl, and 3.22 mg/L ZrOCl$_2$•8H$_2$O.
***GIBCO ® CHEMICALLY DEFINED LIPID CONCENTRATE ("DEFINED LIPID") Catalog No. 11905031 contains 100.0 ml/L ethyl alcohol (200 proof) and 2 mg/L Arachidonic Acid, 220 mg/L Cholesterol, 70 mg/L DL-alpha-Tocopherol Acetate, 0 mg/L Ethyl Alcohol 100%, 10 mg/L Linoleic Acid, 10 mg/L Linolenic Acid, 10 mg/L Myristic Acid, 10 mg/L Oleic Acid, 10 mg/L Palmitic Acid, 10 mg/L Palmitoleic Acid, 90000 mg/L Pluronic F-68, 10 mg/L Stearic Acid, and 2200 mg/L Tween ® 80 (polysorbate 80 sold under the trade name TWEEN 80 by ICI Americas, Inc. Bridgewater, NJ).

Figure 1B:
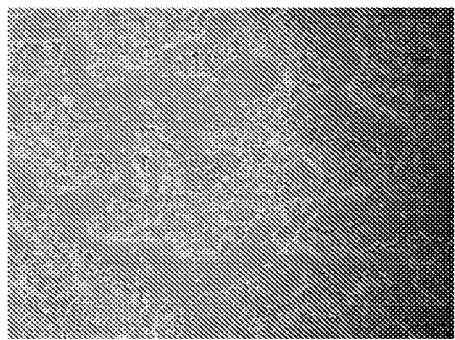
Figure 1C:
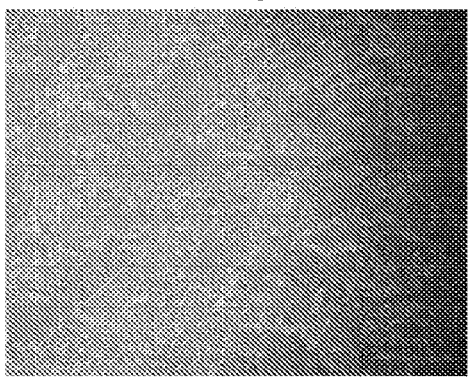
Figure 1D:
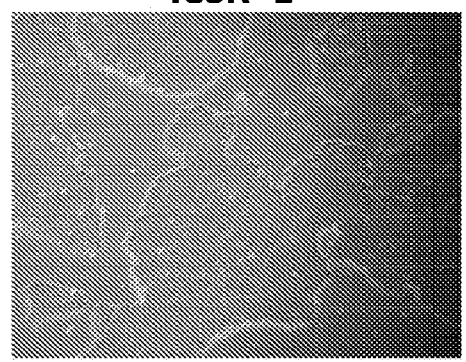

Use of IH-4 and IH-5 were discontinued for further evaluation because cells cultured using IH-4 and IH-5 failed to grow past passage 2. At passage 2, cells grown in IH-2 showed significant change in morphology consistent with differentiated cells and loss of packed colonies. Media IH-1, IH-3, and IH-6 were selected for further evaluation. At passage 3-5, cells cultured in IH-6 showed morphological evidence of differentiated cells at the periphery of the ES colonies (compare FIG. 1C with FIG. 1A, FIG. 1B, and FIG. 1D).

After passage 5, only IH-1 and IH-3 were further compared to the cells cultured in mTeSR®1 media (Catalog No. 05850, Stem-Cell Technologies, Inc., Vancouver BC, Canada). At passages 5 to 18 samples were collected from IH-1, IH-3, and mTeSR®1 cultures and evaluated by FACS, PCR, karyotype analysis (G-banding or FISH), and immune fluorescence staining. The results from FISH analysis are shown in Table II. These results show that H1 cells cultured in IH-1 media or IH-3 media showed normal karyotype, whereas cells cultured in mTeSR®1 media displayed abnormal trisomy 12 at passage 10 and 18.

TABLE II

Results of FISH Analysis of Chromosome 12 and Chromosome 17 by CellLineGenetics (Madison, WI)

| Media | P5 | P10 | P18 |
|---|---|---|---|
| IH-1 | Normal | Normal | Normal |
| IH-3 | Normal | Normal | Normal |
| mTeSR®1 | Normal | 14% Trisomy 12, normal 17 | 14% Trisomy 12, normal 17 |

Figure 2A:
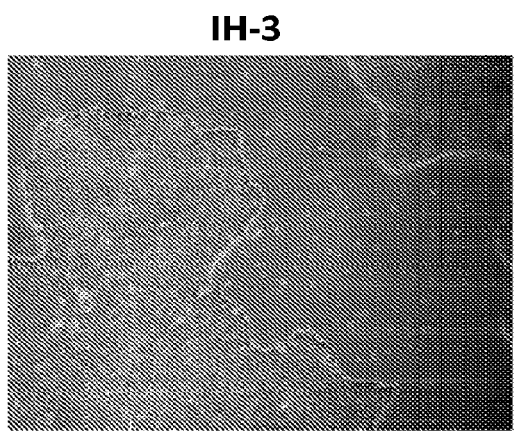
FIG. 2A to FIG. 2C show phase-contrast images of H1 cells cultured for 10 passages in IH-3 (FIG. 2A), IH-1 (FIG. 2B), and mTeSR®1 (FIG. 2C) media.
Figure 2B:
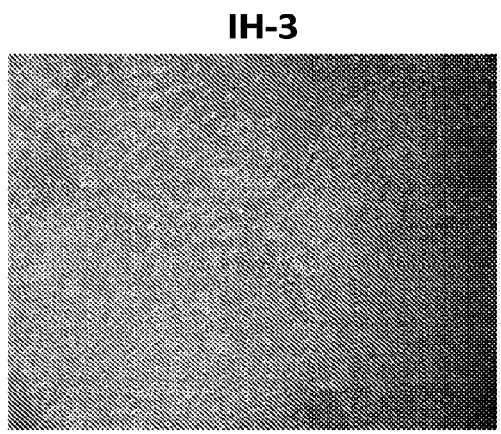
Figure 2C:
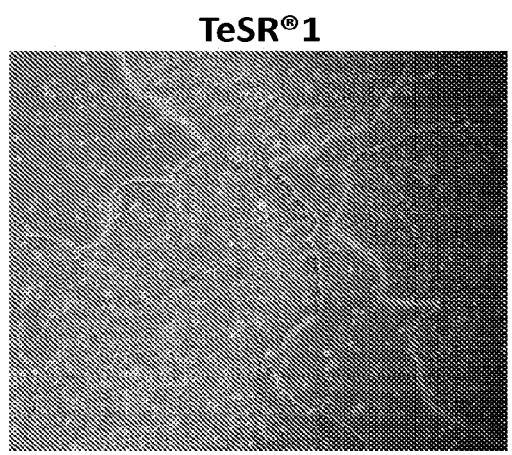
Figure 3A:
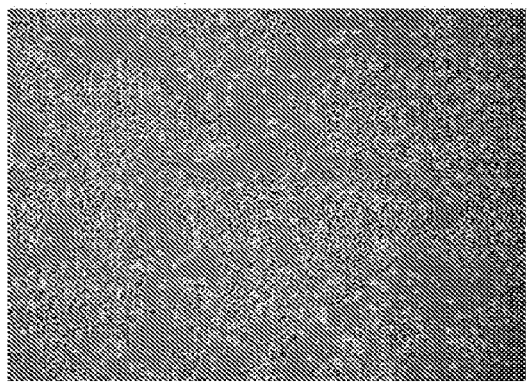
FIG. 3A to FIG. 3C show phase-contrast images of H1 cells cultured for 18 passages in IH-3 (FIG. 3A), IH-1 (FIG. 3B), and mTeSR®1 (FIG. 3C) media.
Figure 3B:
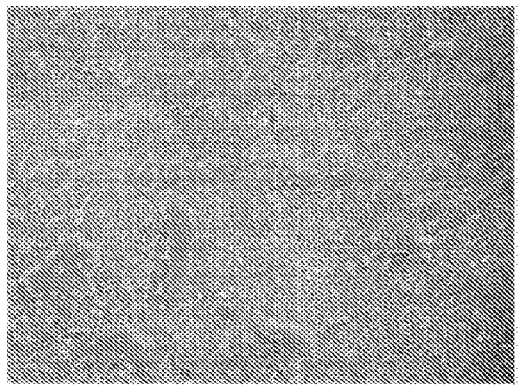
Figure 3C:
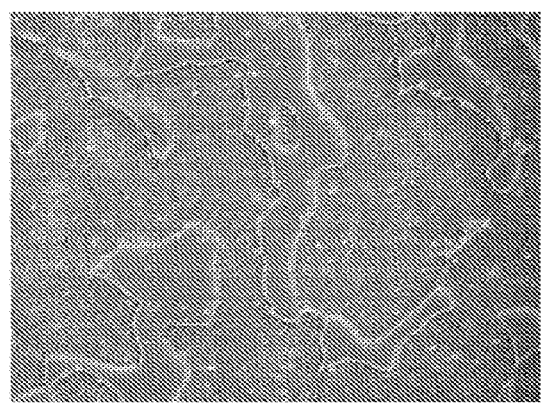
Figure 4A:
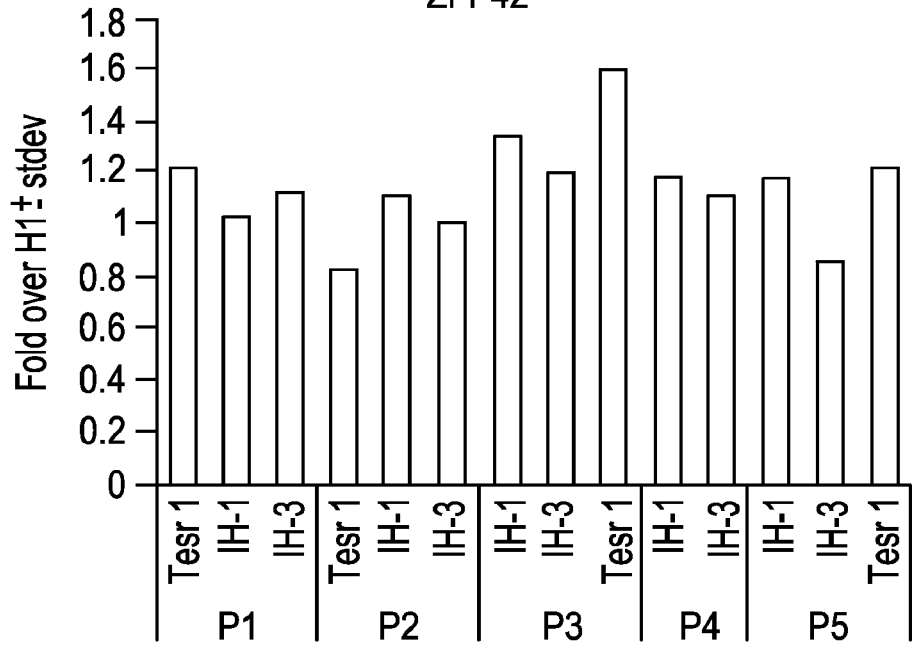
FIG. 4A to FIG. 4F show data from real-time PCR analyses of the expression of the following genes in cells of the human embryonic stem cell line H1 cultured in media described in Example 1 and harvested at passages 1 to 5 (P1-P5); ZFP42 (FIG. 4A), SOX2 (FIG. 4B), POU5F1 (OCT4) (FIG. 4C), Nanog (FIG. 4D), FOXA2 (FIG. 4E), and AFP (FIG. 4F).
Figure 4B:
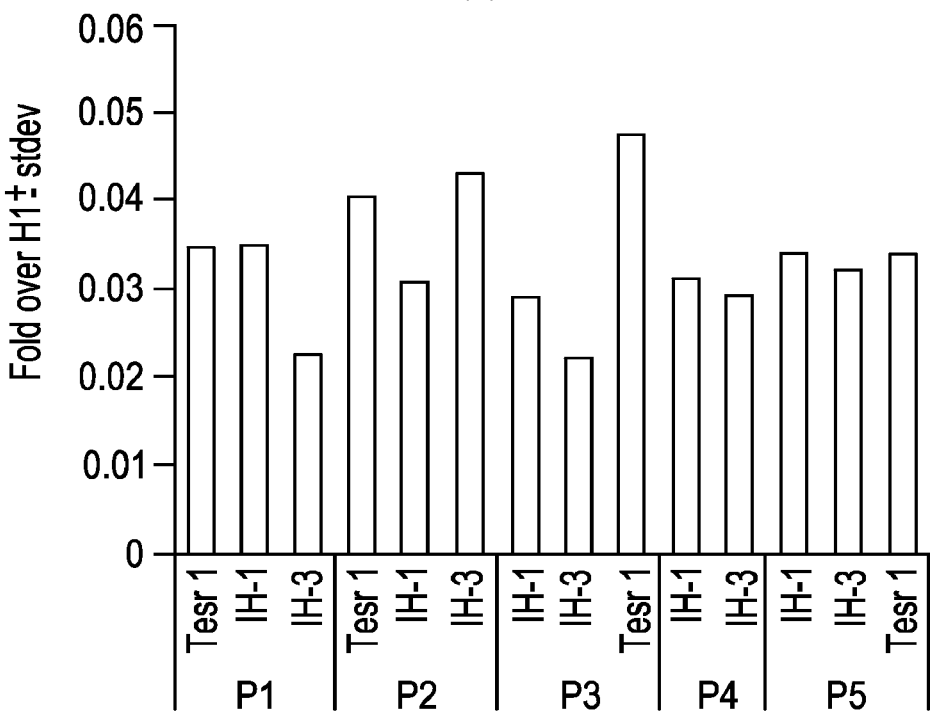
Figure 4C:
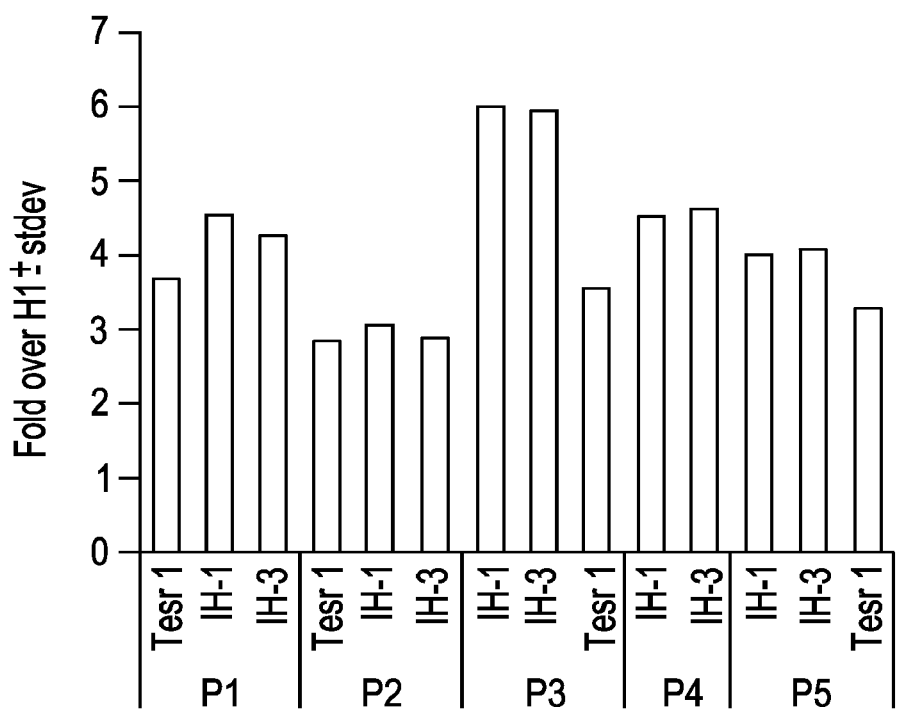
Figure 4D:
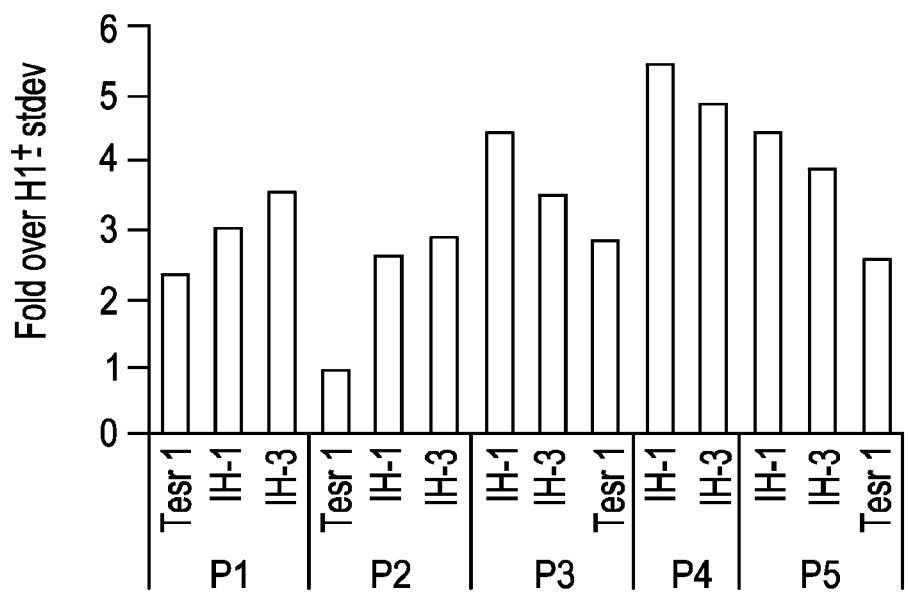
Figure 4E:
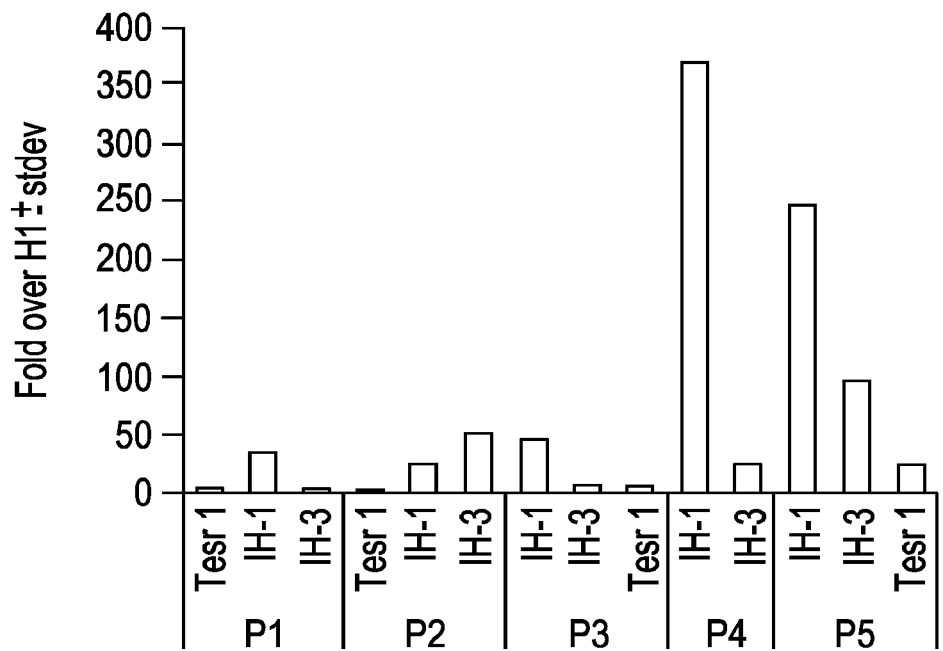
Figure 4F:
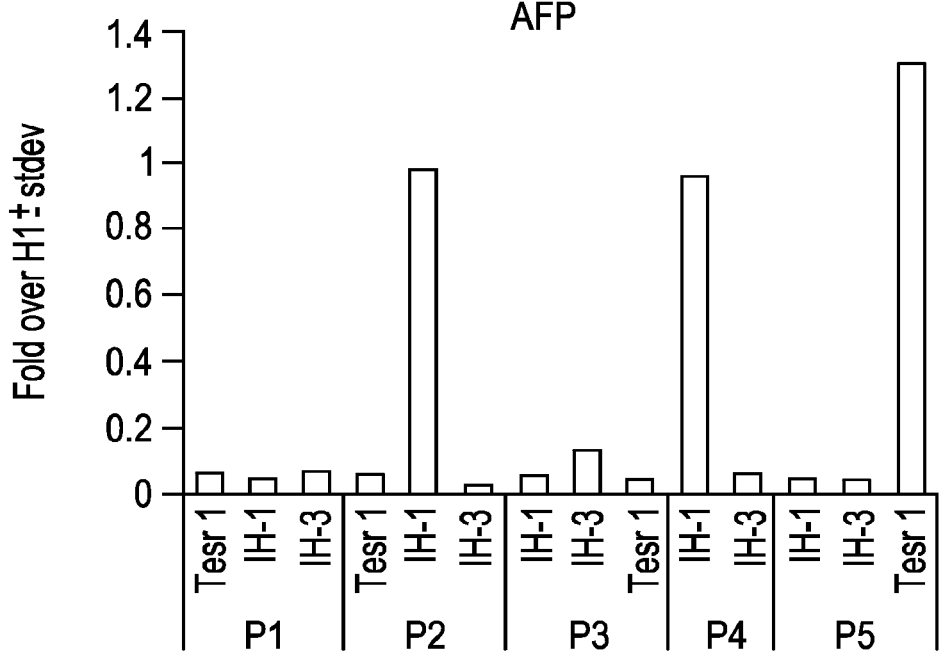

Furthermore, similar to cells grown in mTeSR®1 media, cells passaged continuously in IH-1 media maintained characteristic ES colony morphology with very few differentiated cells surrounding the colonies. However, cells grown in IH-3 media started to lose the characteristic ES colony morphology beyond passage 10 (See FIG. 1A, FIG. 2A, and FIG. 3A).

Evaluation of surface and internal markers attributed to pluripotency was used to assess the impact of the tested formulations on maintenance of pluripotency. As shown in Table III, at passage 5, cells cultured in IH-1 and IH-3 showed similar profile of surface markers as cultures expanded in mTeSR®1 media. However, by passage 10, H1 cells cultured in IH-3 media showed a significant drop in expression of SSEA-4 and a modest drop in expression of TRA1-60 and 1-81. H1 cells cultured in IH-1 media for 10 passages maintained similar expression pattern to those cultured in mTeSR®1 media.

TABLE III

FACS Results at Passage 5 and Passage 10 for Surface Markers Related to the Pluripotency State of the Cells

| | % CD9 | % SSEA-4 | % TRA 1-60 | % TRA 1-81 |
|---|---|---|---|---|
| P5 | | | | |
| IH-1 | 80 | 98 | 50 | 54 |
| IH-3 | 83 | 87 | 39 | 50 |
| mTeSR®1 | 60 | 99 | 56 | 63 |
| P10 | | | | |
| IH-1 | 83 | 95 | 55 | 44 |
| IH-3 | 93 | 15.7 | 42 | 31 |
| mTeSR®1 | 58 | 97 | 55 | 62 |

Surprisingly, similar to H1 cells cultured in mTeSR®1 and IH-1 media, H1 cells cultured in IH-3 media maintained strong expression of OCT4 and SOX2 markers at passage 11 (Table IV). This was despite a very low expression level of SSEA-4 for H1 cells cultured in IH-3 media.

TABLE IV

Internal and surface markers of cells cultured for 11 passages in IH-1, IH-3 and mTeSR ®1 media

| | % Sox2 | % SSEA-4 | % Oct3/4 |
|---|---|---|---|
| IH-1 | 97 | 97 | 92 |
| IH-3 | 98 | 4.2 | 96 |
| mTeSR®1 | 98 | 98 | 92 |

Figure 5A:
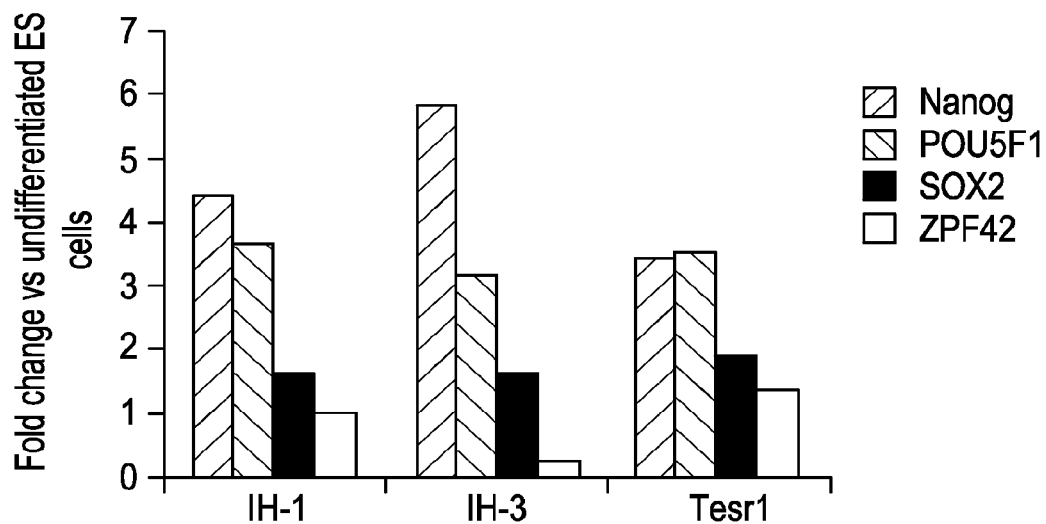
FIG. 5A to FIG. 5B show data from real-time PCR analyses of the expression of Nanog, POU5F1 (OCT4), SOX2, and ZFP42 (FIG. 5A), and of AFP and FOXA2 (FIG. 5B) in cells of the human embryonic stem cell line H1 cultured in media described in Example 1 and harvested at Passage 10.
Figure 5B:
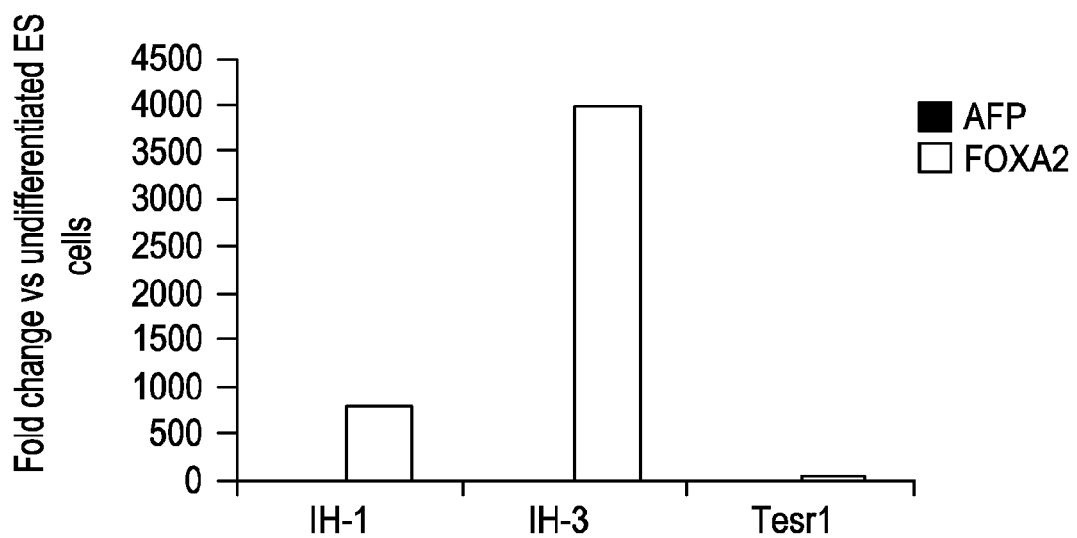
Figure 6A:
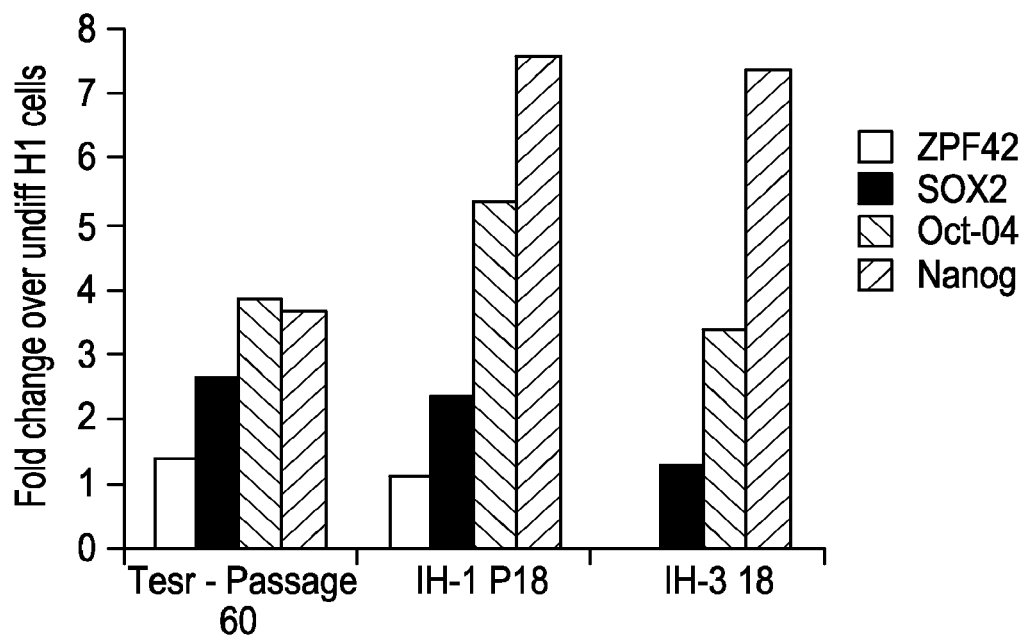
FIG. 6A and FIG. 6B show data from real-time PCR analyses of the expression of ZFP42, SOX2, POU5F1 (OCT4), and Nanog (FIG. 6A), and of AFP and FOXA2 (FIG. 6B) in cells of the human embryonic stem cell line H1 cultured in media described in Example 1 and harvested at Passage 18.
Figure 6B:
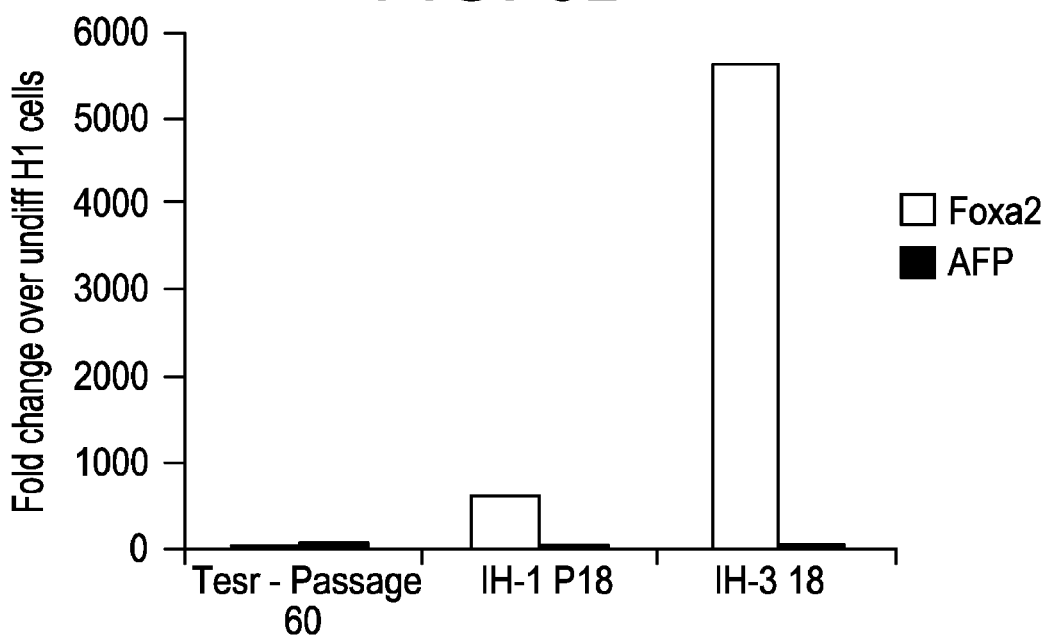
Figure 7A:
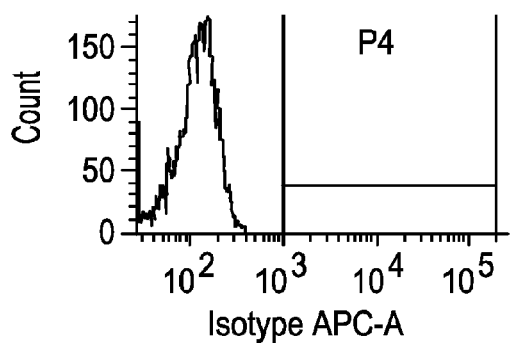
FIG. 7A to FIG. 7F show FACS histogram expression profiles of the following markers in cells cultured for 18 passages in IH-3 media described in Example 1: Isotype control (FIG. 7A); KI-67 (FIG. 7B); OCT4 (FIG. 7C); SOX17 (FIG. 7D); FOXA2 (FIG. 7E); and SOX2 (FIG. 7F). Percentage expression for each marker is shown on each histogram.
Figure 7B:
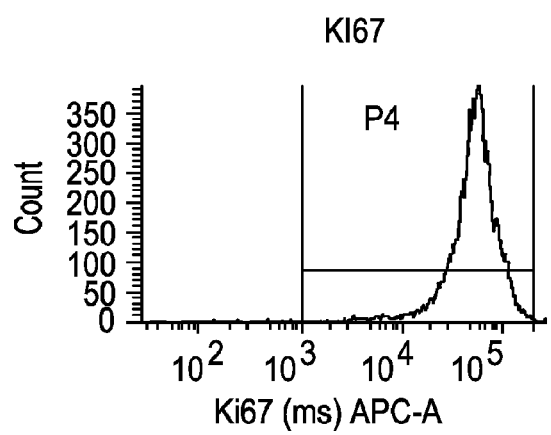
Figure 7C:
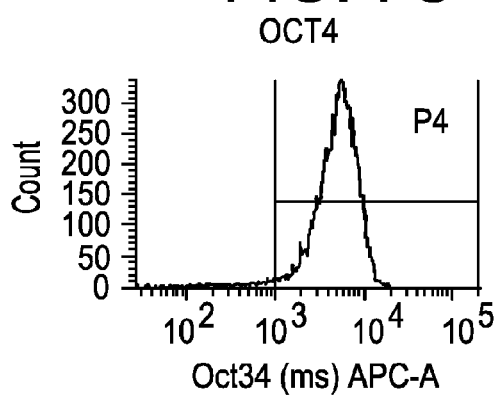
Figure 7D:
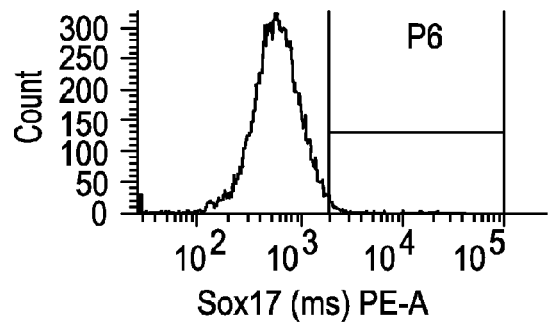
Figure 7E:
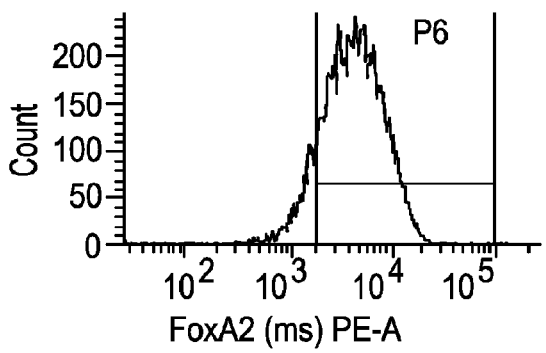
Figure 7F:
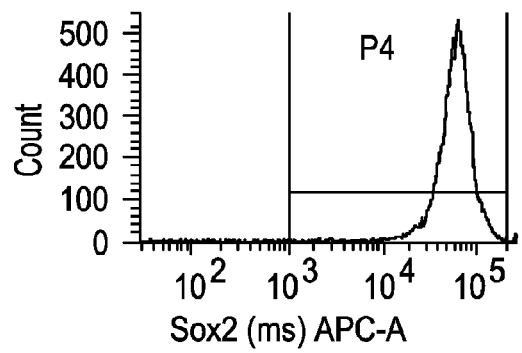
Figure 8A:
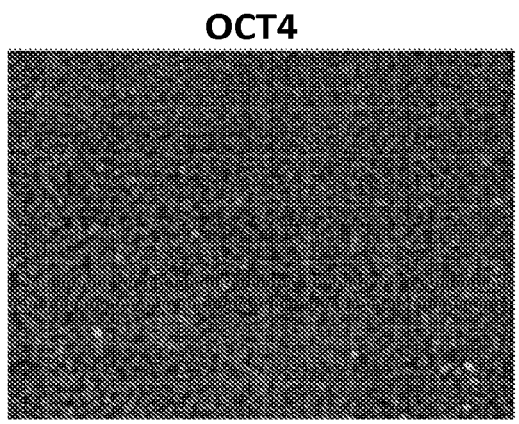
FIG. 8A to FIG. 8F show images of cells cultured for 18 passages in IH-3 media described in Example 1 and immunostained for OCT-4, FOXA2, SOX2, and fluorescent labeling of DNA using DAPI. Images obtained for OCT4 (FIG. 8A), FOXA2 (FIG. 8B), and DAPI-stained DNA (FIG. 8C) were obtained from the same optical field but with different filters. Similarly, images for SOX2 (FIG. 8D), FOXA2 (FIG. 8E), and DAPI stained DNA (FIG. 8F) were obtained from the same optical field but with different filters
Figure 8B:
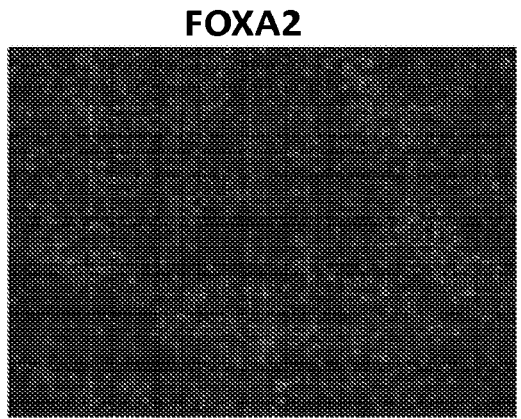
Figure 8C:
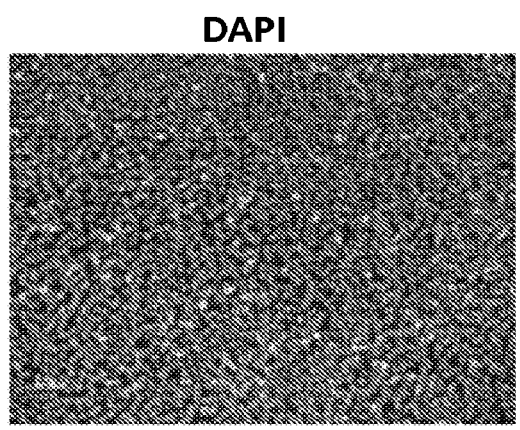
Figure 8D:
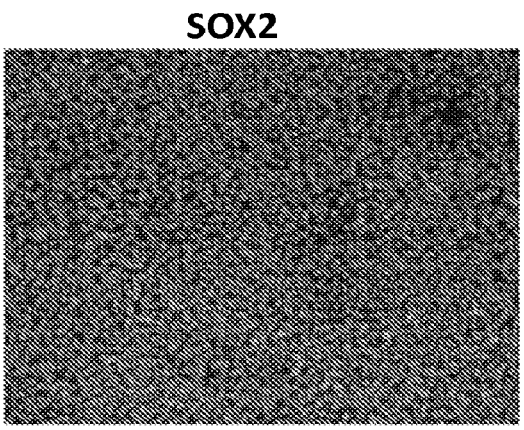
Figure 8E:
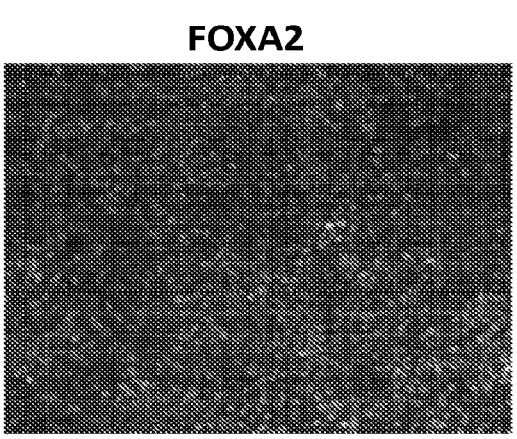
Figure 8F:
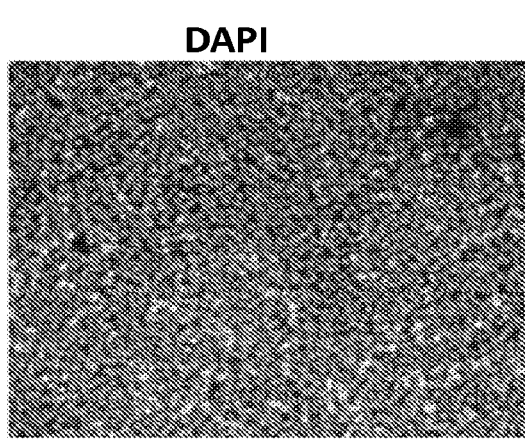

As shown in FIG. 4, mRNA expression of core pluripotency markers, such as Nanog (FIG. 4D), OCT4 (FIG. 4C), SOX2 (FIG. 4B), and ZPF42 (FIG. 4A) were maintained through passage 5 for H1 cells cultured in IH-1, and IH-3 media to the same level as H1 cells cultured in mTeSR®1. However, by passages 10 to 18 there was a significant decrease in expression of ZFP42 while expression of OCT4, Nanog, and SOX2 were not significantly changed for cells grown in IH-3 media as compared to H1 cells cultured in IH-1 or mTeSR®1 media (See FIG. 5A and FIG. 6A). Furthermore, FACS analysis of H1 cells cultured in IH-3 media for 18 passages showed >97% of cells were OCT4+ (FIG. 7C), SOX2+ (FIG. 7F), and KI-67+ (FIG. 7B). Approximately 1% of the cells were SOX17+ (FIG. 7D) and ~85% of the cells were FOXA2+ (FIG. 7E). FIG. 8A to FIG. 8F show images of immunofluorescence staining of H1 cells cultured in IH-3 media for 18 passages. These images illustrate that a significant number of OCT4 and SOX2 positive cells were also FOXA2+. H1 cells cultured in IH3 media had acquired a phenotype where at least 70% of the cells were OCT4+ NANOG+ SOX2+ KI-67+ ZFP42– and FOXA2+. This represents a population of cells not yet described in the art.

EXAMPLE 2

Culturing of H1 Cells in IH-3 Media Spiked with Ascorbic Acid Restores Major Features of Undifferentiated Embryonic Stem Cells In order to identify the cause for the drop in SSEA-4 and ZPF42 for H1 cells cultured in IH-3 vs. those cultured in IH-1 and mTeSR®1 media, a gap analysis was conducted to identify the major reagents present in mTeSR®1 and IH-1 but absent in IH-3 media. IH-3 media was supplemented with TRACE ELEMENTS C Mediatech, Manassas, Va.), ascorbic acid, lithium chloride, or DEFINED LIPID (Invitrogen) as indicated in Table V.

TABLE V

Modifications to IH-3 Media

| Media | Additions to IH-3 Media |
| --- | --- |
| IH-3-1 | 1x TRACE ELEMENTS C |
| IH-3-2 | 0.25 mM ascorbic acid |
| IH-3-3 | 1 mM lithium chloride |
| IH-3-4 | 1:500X DEFINED LIPID |

H1 cells cultured for 14 passages in IH-3 were subsequently cultured in the above media formulations and compared to cells cultured in IH-3 media. At various passages, H1 cells cultured using various media formulations were assayed for pluripotency markers. As shown Table VI, following five additional passages, H1 cells cultured in IH-3-2 (IH-3 supplemented with ascorbic acid) media recovered a small percentage of their SSEA-4 expression as compared to cells cultured in the other tested media.

TABLE VI

FACS Results at Five Passages Beyond Passage 15 for Surface Markers Related to the Pluripotency State of the H1 Cells.

| | CD9 | SSEA-4 |
| --- | --- | --- |
| mTeSR ®1 | 26 | 96.9 |
| IH-1 | 82.9 | 96.9 |
| IH-3 | 89.7 | 0.8 |
| IH-3-1 | 90.4 | 0.9 |
| IH-3-2 | 91.6 | 4.2 |
| IH-3-3 | 87.6 | 0.7 |
| IH-3-4 | 88.8 | 0.6 |

Figure 9A:
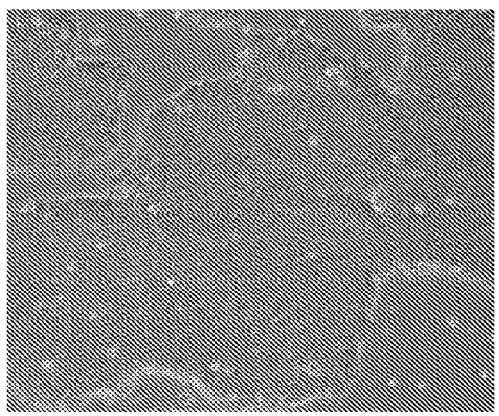
FIG. 9A to FIG. 9F depict phase-contrast images of H1 cells cultured for five passages in mTeSR®1 media (FIG. 9A) and in IH-3 (FIG. 9B), IH-3-1 (FIG. 9C), IH-3-2 (FIG. 9D), IH-3-3 (FIG. 9E), and IH-3-4 (FIG. 9F) formulations described in Example 2.
Figure 9B:
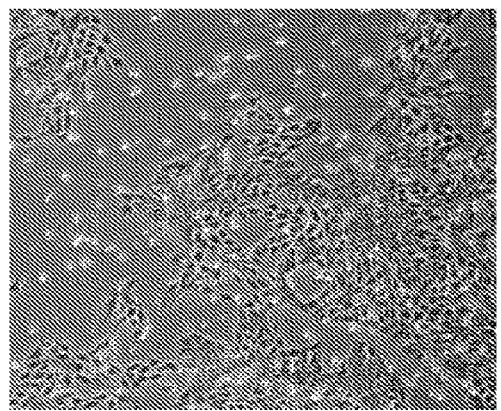
Figure 9C:
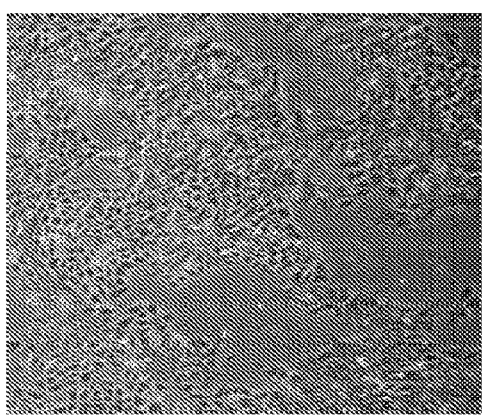
Figure 9D:
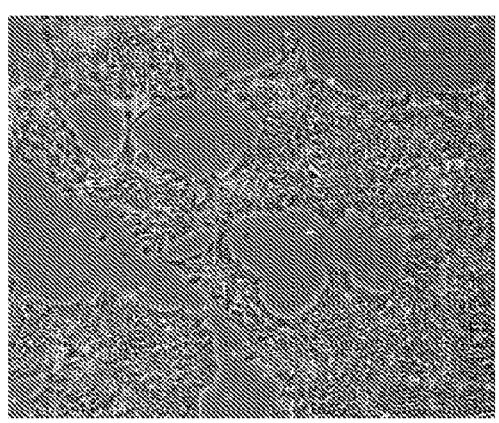
Figure 9E:
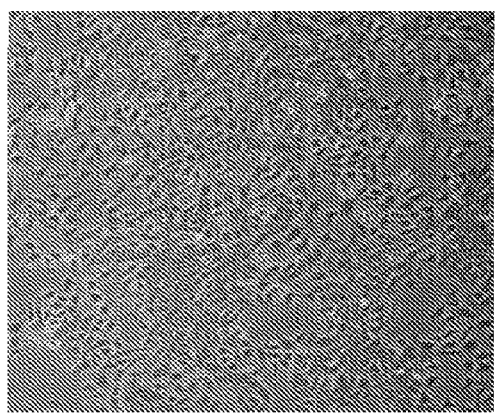
Figure 9F:
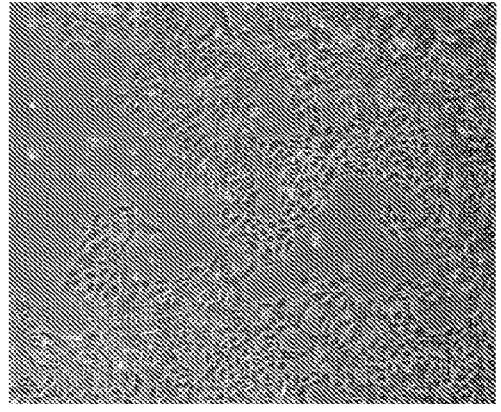
Figure 11A:
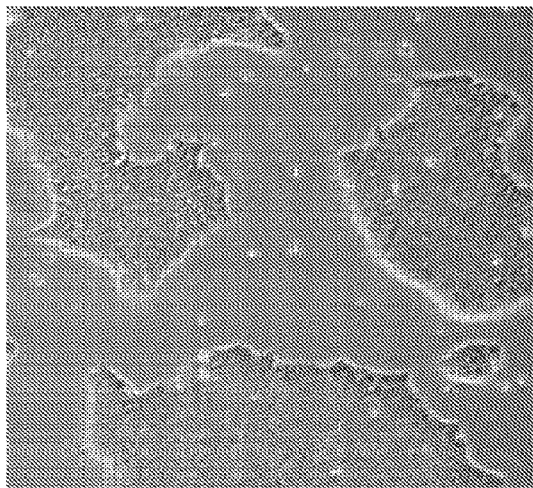
FIG. 11A to FIG. 11D depict phase-contrast images of H1 cells cultured for 20 passages in mTeSR®1 media (FIG. 1A), IH-3 (FIG. 11B), IH-1 (FIG. 11C), and IH-3RT (FIG. 11D) media formulations described in Example 3.
Figure 11B:
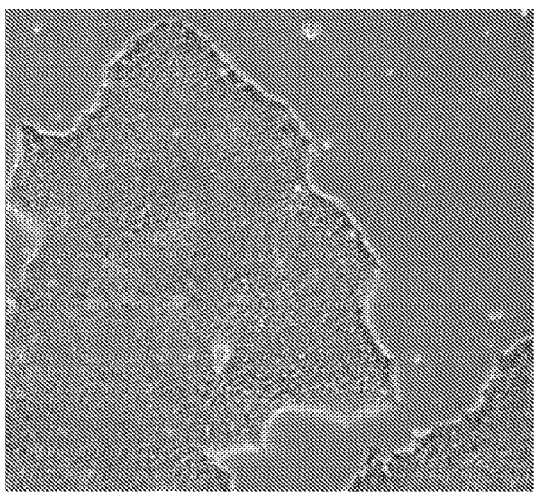
Figure 11C:
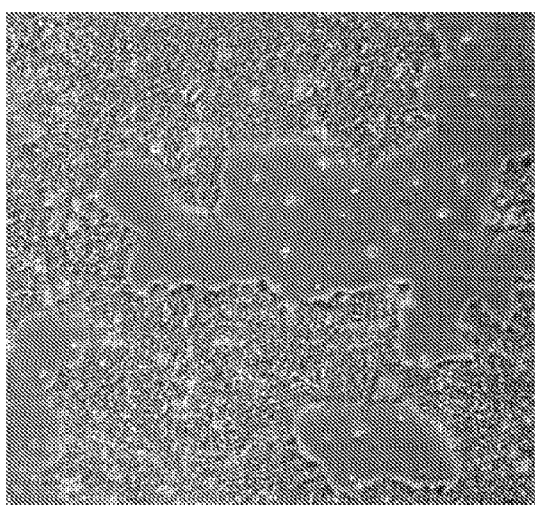
Figure 11D:
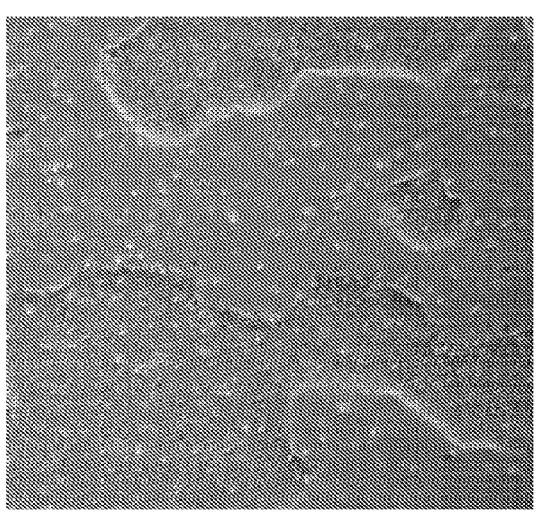
Figure 12A:
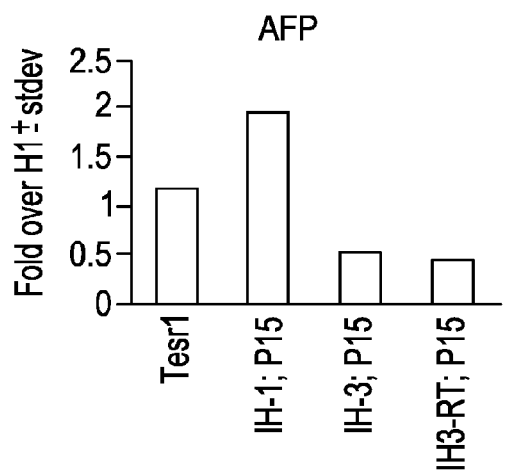
FIG. 12A to FIG. 12F show data from real-time PCR analyses of the expression of the following genes in cells of the human embryonic stem cell line H1 cultured for 15 passages in media described in Example 3: AFP (FIG. 12A), FOXA2 (FIG. 12B), SOX2 (FIG. 12C), Nanog (FIG. 12D), POU5F1 (OCT4) (FIG. 12E), and ZFP42 (FIG. 12F).
Figure 12B:
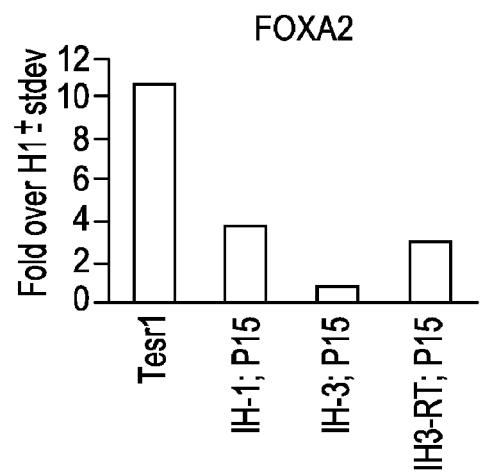
Figure 12C:
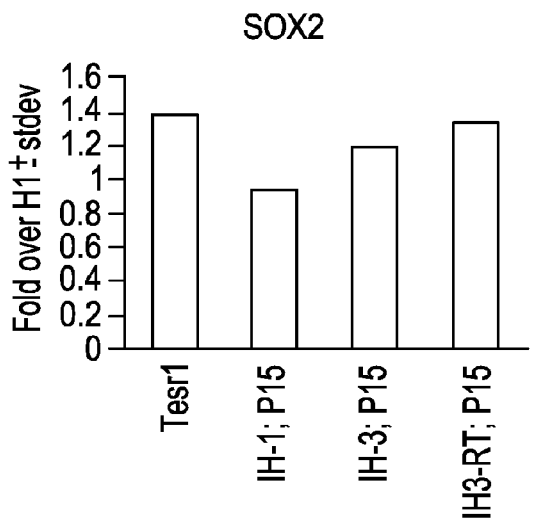
Figure 12D:
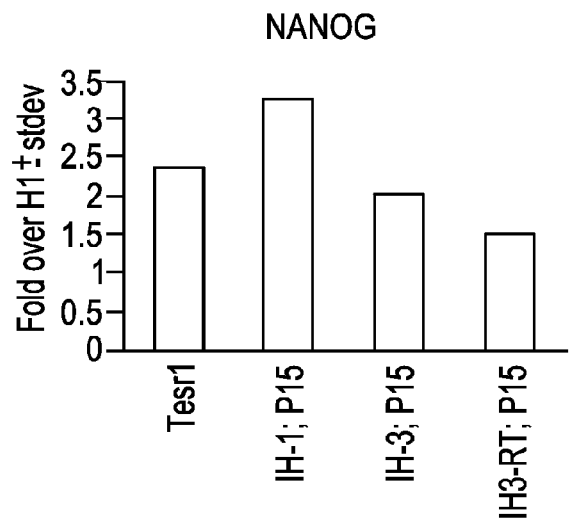
Figure 12E:
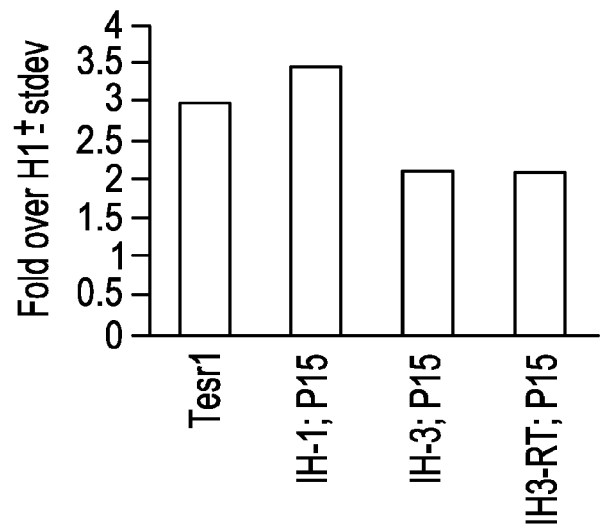
Figure 12F:
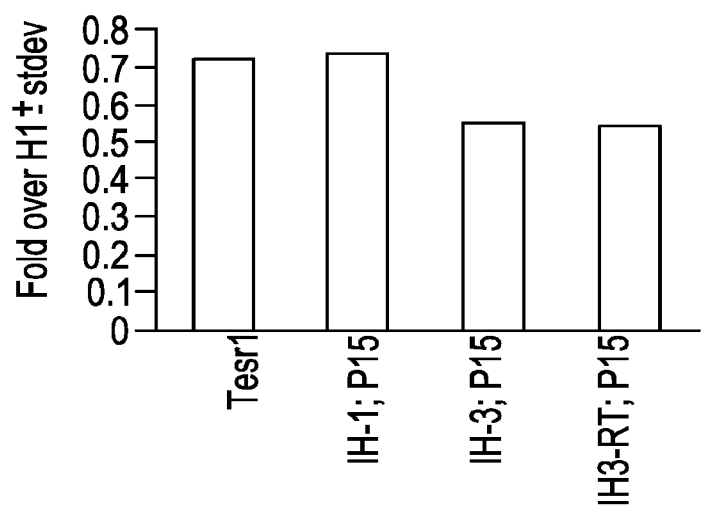

As shown in FIG. 9D, H1 cells cultured in IH-3-2 media retained typical embryonic stem cell morphology similar to cells cultured in mTeSR®1 (FIG. 9A) media. However, H1 cells cultured in IH-3, IH-3-1, IH-3-3, and IH-3-4 showed loose colony morphology (See FIG. 9B, FIG. 9C, and FIG. 9F). PCR analysis of cells cultured in the above media formulations further confirmed that H1 cells cultured in IH-3-2 media regained some of the expression of ZFP42 and down regulated expression of FOXA2 (see FIG. 10A to FIG. 10E). The above data shows that presence of ascorbic acid is required to maintain pluripotency of ES cells along with their characteristic colony/cell morphology and low expression of differentiation markers. Based on this data, subsequent cultures of H1 cells in IH-3 media were further supplemented with 0.25 mM ascorbic acid.

Cells cultured in IH-3-2 recovered some of the characteristic colony morphology of ES cells whereas cells cultured in other IH media formulations displayed a looser morphology.

EXAMPLE 3

Long-Term Cultures of H1 Cells in IH-3 and IH-1 Media Maintain Pluripotency and Stable Karyotype Cells of the human embryonic stem cells line H1 (passage 35 to passage 40), cultured on MATRIGEL™ (1:30 dilution) coated dishes in mTeSR®1 media and passaged using EDTA, as described in Example 1, were used as the starting population to evaluate long-term cultures using IH-1, IH-3-2, IH-3RT and mTeSR®1 media. Cells were passaged as small colonies using 5-10 minute EDTA treatment at room temperature. The components of the tested media are listed in Table VII.

TABLE VII

Ingredients used in IH-1, IH-3-2, and IH-3RT media formulations.

| Media number | Basal Media | Added components* |
| --- | --- | --- |
| IH-1 | MCDB-131 | 1X TRACE ELEMENTS C, 0.25 mM ascorbic acid, 10 mM HEPES, 1 mM lithium chloride, 10 mM D-Glucose, 1:500 X DEFINED LIPID, 1X ITS-X, 2% reagent grade fatty acid free BSA, 1 ng/ml TGF-B1, 100 ng/ml bFGF, 1X GlutaMAX ™ |
| IH-3-2 | DMEM-F12 | 1X ITS-X, 2% reagent-grade fatty acid free BSA, 1 ng/ml TGF-B1, 100 ng/ml bFGF, 20 ng/ml IGF-1, 0.25 mM ascorbic acid |
| IH-3RT | DMEM-F12 | 2% reagent-grade fatty acid free BSA, 1 ng/ml TGF-B1, 100 ng/ml bFGF, 20 ng/ml IGF-1, 0.25 mM ascorbic acid, 5.5 µg/ml Recombinant Human Transferrin (Catalog No. 9701-10, EMD Millipore Corporation, Billerica, MA), 10 µg/ml insulin (Life Technologies Corporation, Carlsbad, CA), 0.0067 µg/ml sodium selenite (Life Technologies Corporation, Carlsbad, CA) |

As seen in FIG. 11A to FIG. 11D, H1 cells cultured for 20 passages in IH-1, IH-3-2, and IH-3RT retained typical ES morphology. The results of PCR analysis of H1 cells cultured for 15 passages in IH-1, IH-3-2, and IH-3RT are shown in FIG. 12A to FIG. 12F. The results of PCR analysis of H1 cells cultured for 20 passages in IH-1, IH-3-2, and IH-3RT are shown in FIG. 13A to FIG. 13F. These analyses confirmed that, similar to H1 cells cultured in mTeSR®1 media, cells cultured for 15 or 20 passages in IH-1, IH-3-2, and IH-3RT (recombinant human transferrin) media retained all core pluripotency markers while showing very low expression of FOXA2 and AFP. FACS analysis at Passage 15 and Passage 20 also confirmed expression of surface markers related to pluripotent cells to the same levels as H1 cells cultured in mTeSR®1 media (See Table VIII).

TABLE VIII

FACS Results for Cells Tested at Passage 15 and Passage20 for Surface Markers Related to the Pluripotency State of the Cells

| | % CD9 | % SSEA-4 | % TRA 1-60 | % TRA 1-81 |
|---|---|---|---|---|
| | | P15 | | |
| IH-1 | 93 | 99 | 59 | 59 |
| IH-3-2 | 72 | 99 | 55 | 52 |
| IH-3RT | 65 | 99 | 50 | 48 |
| mTeSR®1 | 63 | 99 | 49 | 49 |
| | | P20 | | |
| IH-1 | 91 | 96 | 52 | 54 |
| IH-3-2 | 91 | 99 | 49 | 53 |
| mTeSR®1 | 66 | 97 | 57 | 63 |

H1 cells cultured continuously in IH-1, IH-3-2, and IH-3RT showed normal karyotype as measured by G-banding and FISH analysis. However, H1 cells cultured for 10 to 20 passages in mTeSR®1 showed abnormal chromosomal counts (See Table IX).

TABLE IX

FISH and G-banding Analysis of H1 Cells Cultured in IH-1, IH-3, IH-3RT, and mTeSR® 1.

| Media | P10 (G-banding and FISH) | P15 (FISH) | P20 (FISH) |
|---|---|---|---|
| IH-1 | 46 XY, Normal 12 and 17 chromosomes | Normal | Normal |
| IH-3-2 | 46 XY, Normal 12 and 17 chromosomes | Normal | Normal |
| IH-3RT | 46 XY, Normal 12 and 17 chromosomes | Normal | ND |
| mTeSR® 1 | 48, XY, +12, +14[2], /46, XY[18]-20% trisomy 12 by FISH | 11% Trisomy 12, normal 17 | 20% Trisomy 12, normal 17 |

Example 4

Equivalent Proliferation Rate for H1 Cells Cultured in IH-1, IH-3, and mTeSR®1 Media In order to compare the proliferation rate of cells cultured in previously tested media, H1 cells cultured in IH-1, IH-3-2 and mTeSR®1 media were released by using TrypLE (Invitrogen) and seeded at a density of $5 \times 10^5$ cells per 10 cm MATRIGEL™-coated dishes. In order to reduce apoptosis of single cells and enhance attachment, released cells were pretreated with 10 µM Rock inhibitor (Sigma). Media was changed daily until three days post-seeding. On day 3, cells were released as single cells and counted using a hemocytometer. As shown in Table X, cells cultured in all three media formulations showed equivalent doubling times.

TABLE X

Doubling Times of H1 Cells Cultured in mTeSR ®1, IH-1, and IH-3-2 Media Formulations.

| | mTeSR ® 1 | IH-1 | IH-3-2 |
|---|---|---|---|
| 0 h | $0.5 \times 10^6$ cells | $0.5 \times 10^6$ cells | $0.5 \times 10^6$ cells |
| 72 h | $6.7 \times 10^6$ cells | $4.2 \times 10^6$ cells | $6.8 \times 10^6$ cells |
| Cell Doubling Time | 19.23 h | 23.45 h | 19.12 h |

Example 5

High Quality Fatty-Acid Free BSA Allows for Expansion of Pluripotent Cells

Figure 14A:
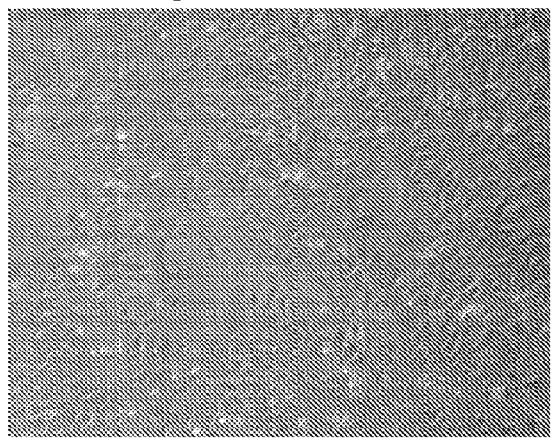
FIG. 14A and FIG. 14B depict phase-contrast images of H1 cells cultured for 4 days in media formulations described in Example 5 containing Sigma BSA (FIG. 14A) or containing fatty acid free BSA (FIG. 14B).
Figure 14B:
Figure 15A:
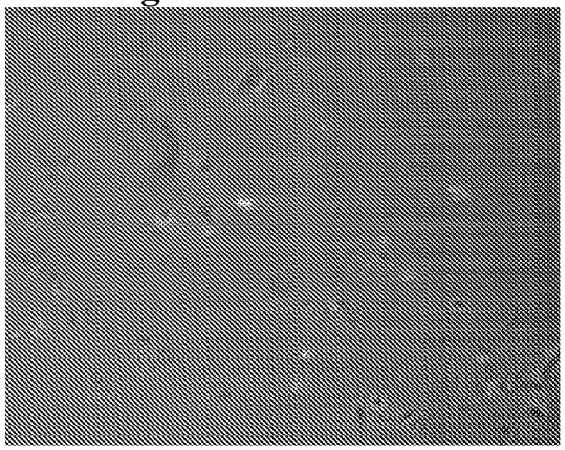
FIG. 15A and FIG. 15B depict phase-contrast images of H1 cells cultured for three passages in media formulations described in Example 5 containing Sigma BSA (FIG. 15A) or containing fatty acid free BSA (FIG. 15B).
Figure 15B:
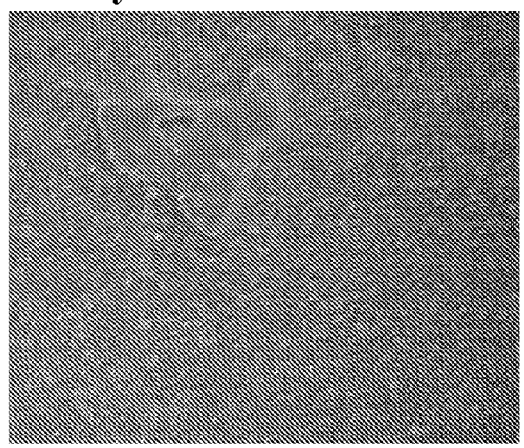

Cells of the human embryonic stem cells line H1 (passage 35 to passage 40), cultured on MATRIGEL™ (1:30 dilution) coated dishes in mTeSR®1 media and passaged using EDTA, were used as the starting population to evaluate short-term cultures using IH-3-2 media supplemented with either 2% Sigma BSA (catalog No. A2153; Lot: 061M1804V, Sigma Aldrich Co LLC, Saint Louis, Mo.) or fatty-acid free BSA (Catalog No. 7500804; Lot: 11G54001, LAMPIRE Biological Laboratories, Inc., Pipersville, Pa.). Cells were passaged as small colonies using 5-10 minute EDTA treatment at room temperature. FIG. 14A and FIG. 14B depict phase-contrast images of H1 cells cultured for 4 days in media formulations containing Sigma BSA (FIG. 14A) or fatty acid free BSA (FIG. 14B). FIG. 15A and FIG. 15B depict phase-contrast images of H1 cells cultured for three passages in media formulations containing Sigma BSA (FIG. 15A) or fatty acid free BSA (FIG. 15B). As seen in FIG. 14A, as early as day 4 following seeding, there was morphological evidence of differentiated cells in cultures using Sigma BSA. However, there was no gross differentiated cell morphology evident in cultures treated with fatty acid-free BSA (see FIG. 14B)). The same trend was noted at passage 3, there was morphological evidence of differentiated cells in cultures using Sigma BSA (see FIG. 15A), while there was no gross differentiated cell morphology evident in cells cultured in media comprising fatty acid-free BSA (see FIG. 15B). Furthermore, there was a significant drop in confluency of cells cultured in media comprising Sigma BSA as compared to cells cultured in media comprising reagent grade fatty-acid BSA (compare FIG. 15A and FIG. 15B).

Figure 16A:
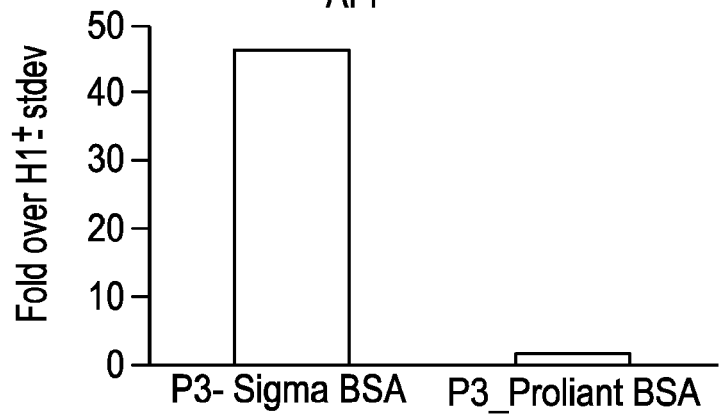
FIG. 16A to FIG. 16C show data from real-time PCR analyses of the expression of the following genes in cells of the human embryonic stem cell line H1 cultured for three passages in media formulations described in Example 5 containing Sigma BSA or fatty acid free BSA: AFP (FIG. 16A), MIXL1 (FIG. 16B), and T (BRY) (FIG. 16C).
Figure 16B:
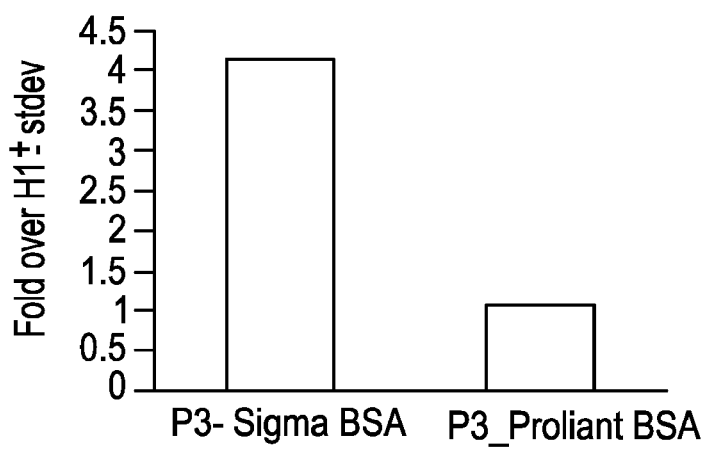
Figure 16C:
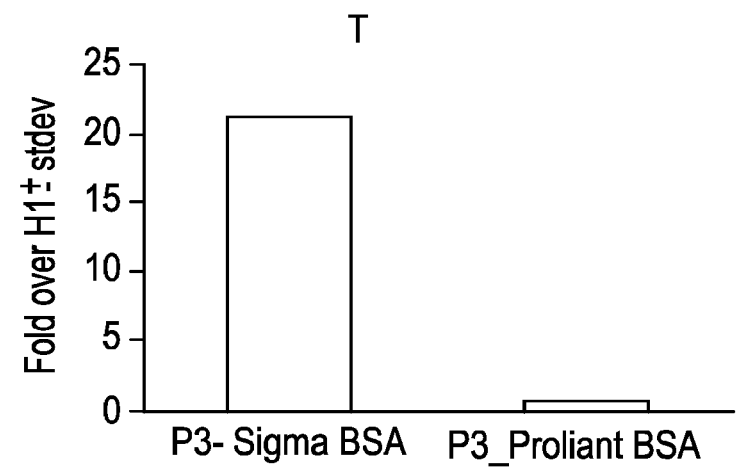
Figure 18A:
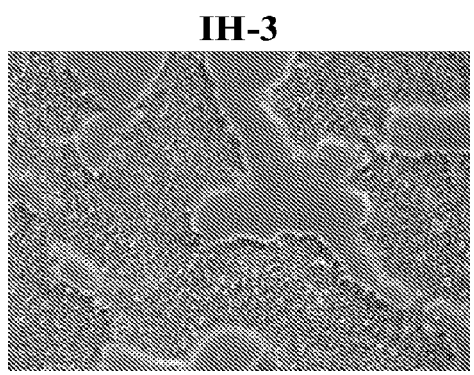
FIG. 18A to FIG. 18E depict phase-contrast images of H1 cells cultured for 10 passages in IH-3 (FIG. 18A), IH-3P-2 (FIG. 18B), IH-3P-3 (FIG. 18C), IH-3P-4 (FIG. 18D), and IH-3P-5 (FIG. 18E) media formulations described in Example 6.
Figure 18B:
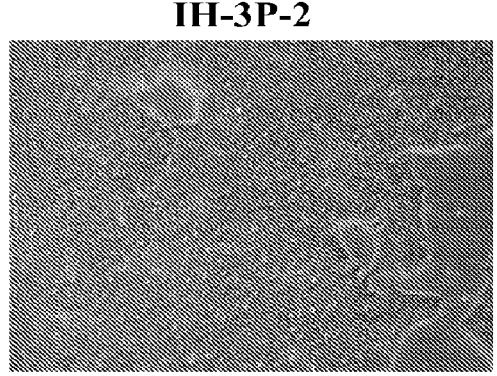
Figure 18C:
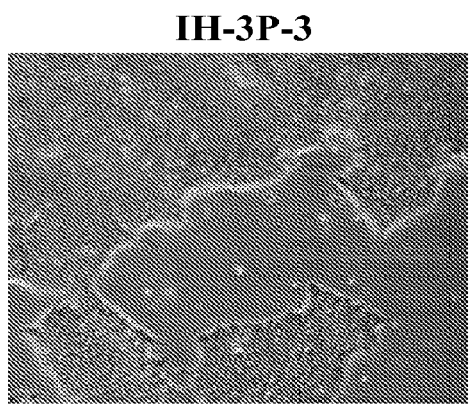
Figure 18D:
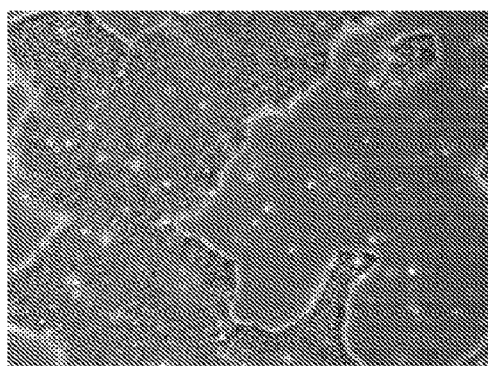
Figure 18E:
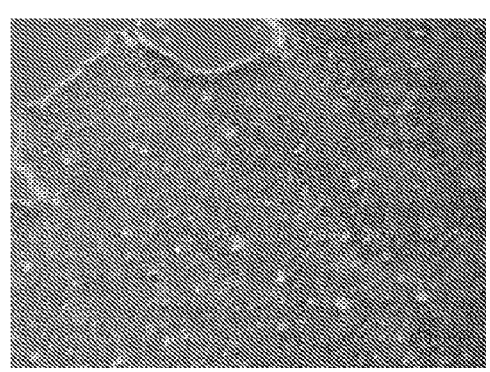

Data from real-time PCR analyses of the expression of AFP (FIG. 16A), MIXL1 (FIG. 16B), and T (BRY) (FIG. 16C) in cells of the human embryonic stem cell line H1 cultured for three passages in media formulations containing Sigma BSA or fatty acid free BSA are shown in FIGS. 16A, 16B, and 16C. PCR data at passage 3 clearly showed significant upregulation of markers associated with a differentiated cell for cells cultured in media comprising Sigma BSA. This data clearly demonstrates that use of fatty-acid-free BSA is critical in the maintenance of pluripotency, colony morphology, and proliferation of cells.

Example 6

Pluripotent Stem Cells can be Propagated and Maintain Pluripotency in IH-3 Media Using a Wide Range of Fatty Acid Free BSA and bFGF Concentrations Cells of the human embryonic stem cells line H1 (passage 35 to passage 40), cultured on MATRIGEL™ (1:30 dilution) coated dishes in mTeSR®1 media and passaged using EDTA, were used as the starting population to evaluate short and long-term cultures using IH-3 media supplemented as indicated in Table XI.

TABLE XI

Ingredients used in IH-3 media supplemented with varying doses of BSA and bFGF

| Media number | Basal Media | Added components* |
|---|---|---|
| IH-3-2 | DMEM-F12 | 1X ITS-X, 2% reagent-grade fatty acid free BSA, 1 ng/ml TGF-B1, 100 ng/ml bFGF, 20 ng/ml IGF-1, 0.25 mM ascorbic acid |
| IH-3P-2 | DMEM-F12 | 1X ITS-X, 2% reagent-grade fatty acid free BSA, 1 ng/ml TGF-B1, 50 ng/ml bFGF, 20 ng/ml IGF-1, 0.25 mM ascorbic acid |
| IH-3P-3 | DMEM-F12 | 1X ITS-X, 1% reagent-grade fatty acid free BSA, 1 ng/ml TGF-B1, 100 ng/ml bFGF, 20 ng/ml IGF-1, 0.25 mM ascorbic acid |
| IH-3P-4 | DMEM-F12 | 1X ITS-X, 0.5% reagent-grade fatty acid free BSA, 1 ng/ml TGF-B1, 100 ng/ml bFGF, 20 ng/ml IGF-1, 0.25 mM ascorbic acid |
| IH-3P-5 | DMEM-F12 | 1X ITS-X, 0% reagent-grade fatty acid free BSA, 1 ng/ml TGF-B1, 100 ng/ml bFGF, 20 ng/ml IGF-1, 0.25 mM ascorbic acid |

At passage 10, cells were evaluated morphologically by PCR for pluripotency and differentiation-associated genes. Furthermore, cells were evaluated for karyotypic stability using FISH analysis for chromosomes 12 and 17. FIG. 17A to FIG. 17D show data from real-time PCR analyses of the expression of SOX2 (FIG. 17A), POU5F1 (FIG. 17B), NANOG (FIG. 17C), and FOXA2 (FIG. 17C) in cells of the human embryonic stem cell line H1 cultured for ten passages in media formulations listed in Table XI. As shown in these figures, all of the above formulations retained strong expression of pluripotency markers relative to cells grown in mTeSR®1 media. However, cells grown in 0-0.5% BSA showed higher expression of FOXA2 indicating a higher level of spontaneous differentiation in these cultures as compared to the other tested formulations. FIG. 18A to FIG. 18E depict phase-contrast images of H1 cells cultured for 10 passages in IH-3-2 (FIG. 18A), IH-3P-2 (FIG. 18B), IH-3P-3 (FIG. 18C), IH-3P-4 (FIG. 18D), and IH-3P-5 (FIG. 18E) media formulations listed in Table XI. As indicated in these figures, all formulations tested in this example allowed for formation of ES colonies with minimal evidence of gross differentiated morphology.

TABLE XII

FISH analysis of chromosome 12 and 17 analyzed by Cell Line Genetics

| Media | P10 |
|---|---|
| IH-3-2 | Normal |
| IH-3P-2 | Normal |
| IH-3P-3 | Normal |
| IH-3P-4 | Normal |
| IH-3P-5 | Normal |

As seen in Table XII, H1 cells cultured for ten passages in media formulations listed in Table XI retained normal counts for chromosome 12 and 17 as measured by FISH analysis. The above data indicates that defined media consisting of DMEM/F12 basal media supplemented with ITS-X, reagent-grade fatty acid-free BSA, TGF-B1, IGF-1, and ascorbic acid allows for expansion of pluripotent cells while maintaining pluripotency of the cells when using a wide range of concentrations of fatty acid-free BSA and bFGF.

What is claimed is:

1. A method for expanding human pluripotent stem cells comprising culturing the human pluripotent stem cells on a feeder-free matrix in a defined cell culture formulation,
   wherein the defined cell culture formulation consists essentially of DMEM-F12 basal medium, insulin, transferrin, selenium, fatty-acid free albumin, from about 0.5 ng/ml to about 10 ng/ml of a TGF-β ligand, from about 50 ng/ml to about 100 ng/ml of bFGF, and from about 10 ng/ml to about 50 ng/ml of IGF-1, and
   wherein culturing the human pluripotent stem cells in the defined cell culture formulation maintains the pluripotency and karyotypic stability of the cells for at least 10 passages.

2. The method of claim 1, wherein the TGF-β ligand is TGF-β1.

3. The method of claim 1, wherein the fatty acid free albumin is reagent grade.

4. The method of claim 1, wherein at least 80% of the cells express CD9 at five passages beyond passage 15.

5. The method of claim 1, wherein the defined culture formulation consists of DMEM F-12 basal medium, insulin, transferrin, selenium, fatty-acid free albumin, a TGF-β ligand, bFGF, and IGF-1.

6. The method of claim 1, wherein the defined culture formulation consists of DMEM F-12 basal medium, insulin, transferrin, selenium, fatty-acid free albumin, TGF-β1, bFGF, and IGF-1.

7. The method of claim 1, wherein the human pluripotent stem cells are human embryonic stem cells.

8. The method of claim 1, wherein the defined cell culture formulation lacks ascorbic acid.

9. The method of claim 1, wherein the defined cell culture formulation consists essentially of about 1 ng/ml of TGF-β1.

10. The method of claim 1, wherein the defined cell culture formulation consists essentially of about 100 ng/ml of bFGF.

11. The method of claim 1, wherein the defined cell culture formulation consists essentially of about 20 ng/ml of IGF-1.

12. The method of claim 1, wherein the defined cell culture formulation consists essentially of DMEM-F12 basal medium, insulin, transferrin, selenium, fatty-acid free albumin, about 1 ng/ml of TGF-β1, about 100 ng/ml of bFGF, and about 20 ng/ml of IGF-1.

13. The method of claim 1, wherein the defined cell culture formulation consists of DMEM-F12 basal medium, insulin, transferrin, selenium, fatty-acid free albumin, about 1 ng/ml of TGF-β1, about 100 ng/ml of bFGF, and about 20 ng/ml of IGF-1.

* * * * *